United States Patent
Rapta

(10) Patent No.: US 8,962,864 B2
(45) Date of Patent: Feb. 24, 2015

(54) PROCESS FOR PREPARING 4-AMINO-5-BIPHENYL-4-YL-2-HYDROXYMETHYL-2-METHYL-PENTANOIC ACID COMPOUNDS

(71) Applicant: Miroslav Rapta, San Carlos, CA (US)

(72) Inventor: Miroslav Rapta, San Carlos, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 17 days.

(21) Appl. No.: 13/767,581

(22) Filed: Feb. 14, 2013

(65) Prior Publication Data

US 2013/0211098 A1    Aug. 15, 2013

Related U.S. Application Data

(60) Provisional application No. 61/599,020, filed on Feb. 15, 2012.

(51) Int. Cl.

| | |
|---|---|
| *C07D 295/00* | (2006.01) |
| *C07D 207/00* | (2006.01) |
| *C07D 405/12* | (2006.01) |
| *C07D 207/20* | (2006.01) |
| *C07D 309/12* | (2006.01) |
| *C07D 407/12* | (2006.01) |
| *C07D 405/14* | (2006.01) |
| *C07D 207/277* | (2006.01) |
| *C07D 317/34* | (2006.01) |
| *C07D 319/06* | (2006.01) |
| *C07D 249/10* | (2006.01) |
| *C07D 207/263* | (2006.01) |

(52) U.S. Cl.
CPC ............ *C07D 405/12* (2013.01); *C07D 207/20* (2013.01); *C07D 309/12* (2013.01); *C07D 407/12* (2013.01); *C07D 405/14* (2013.01); *C07D 207/277* (2013.01); *C07D 317/34* (2013.01); *C07D 319/06* (2013.01); *C07D 249/10* (2013.01); *C07D 207/263* (2013.01)
USPC .......................................... 548/531; 548/551

(58) Field of Classification Search
None
See application file for complete search history.

(56) References Cited

U.S. PATENT DOCUMENTS

| 8,481,044 B2* | 7/2013 | Fleury et al. ............... 424/184.1 |
| 2010/0113801 A1 | 5/2010 | Hook et al. |
| 2012/0213806 A1 | 8/2012 | Fleury et al. |

FOREIGN PATENT DOCUMENTS

WO    2010/136493 A1    12/2010

OTHER PUBLICATIONS

Wittenberger et al., "The Design and synthesis of cyclic renin inhibitors", Tetrahedron Letters, 32(52):7655-7658 (1991).
PCT International Search Report for PCT/US2013/026182 dated May 6, 2013.

* cited by examiner

*Primary Examiner* — Kamal Saeed
(74) *Attorney, Agent, or Firm* — Jeffrey A. Hagenah; Shelley Eberle

(57) ABSTRACT

The invention provides processes for preparing intermediates useful for preparing compounds of the formula:

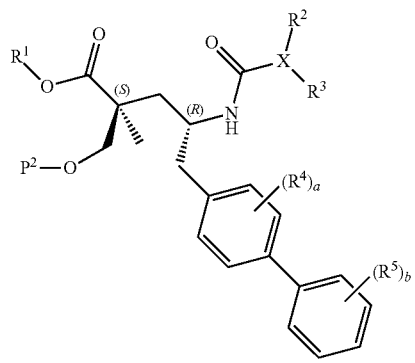

or a tautomer or salt thereof, where $R^1$-$R^5$, a, b, X and $P^2$, are as defined in the specification.

12 Claims, No Drawings

PROCESS FOR PREPARING 4-AMINO-5-BIPHENYL-4-YL-2-HYDROXYMETHYL-2-METHYL-PENTANOIC ACID COMPOUNDS

CROSS-REFERENCE TO RELATED APPLICATIONS

This application claims the benefit of U.S. Provisional Application No. 61/599,020, filed on Feb. 15, 2012; the entire disclosure of which is incorporated herein by reference.

BACKGROUND OF THE INVENTION

1. Field of the Invention

The present invention relates to processes and intermediates for preparing 4-amino-5-biphenyl-4-yl-2-hydroxymethyl-2-methyl-pentanoic acid compounds that are useful in preparing compounds having neprilysin-inhibition activity.

2. State of the Art

Commonly-assigned U.S. Patent Application Publication 2012/0213806 to Fleury et al., discloses compounds that have activity as neprilysin inhibitors, the disclosure of which is incorporated herein by reference. In one embodiment, this application discloses compounds such as (2S,4R)-5-biphenyl-4-yl-2-hydroxymethyl-2-methyl-4-[(3H-[1,2,3]triazole-4-carbonyl)-amino]-pentanoic acid 5-methyl-2-oxo-[1,3]dioxol-4-ylmethyl ester and its tautomer (2S,4R)-5-biphenyl-4-yl-2-hydroxymethyl-2-methyl-4-[(1H-[1,2,3]triazole-4-carbonyl)-amino]-pentanoic acid 5-methyl-2-oxo-[1,3]dioxol-4-ylmethyl ester.

When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point, which allows the material to be processed without significant decomposition. A crystalline form of (2S,4R)-5-biphenyl-4-yl-2-hydroxymethyl-2-methyl-4-[(1H-[1,2,3]triazole-4-carbonyl)-amino]pentanoic acid 5-methyl-2-oxo-[1,3]dioxol-4-ylmethyl ester is disclosed in commonly-assigned U.S. Provisional Application No. 61/599,023, filed on Feb. 15, 2012, and entitled "Crystalline Form of (2S,4R)-5-Biphenyl-4-yl-2-hydroxymethyl-2-methyl-4-[(1H-[1,2,3]triazole-4-carbonyl)amino]pentanoic Acid 5-Methyl-2-oxo-[1,3]dioxol-4-ylmethyl Ester", the disclosure of which is incorporated herein by reference.

The compounds disclosed in these publications and applications are prepared by techniques that typically require a diastereomically pure starting material and where one or more intermediates are purified by chromatography. There are several advantages to developing processes where such purification steps are not necessary. This invention addresses that need.

SUMMARY OF THE INVENTION

The present invention relates to intermediates and improved processes for preparing intermediates useful for preparing compounds of formula IV

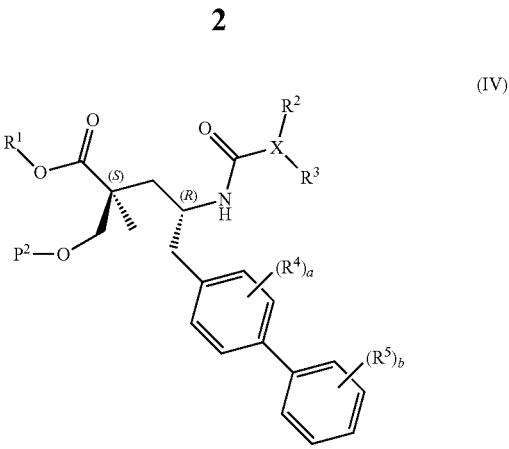

or a tautomer or salt thereof, where $R^1$-$R^5$, a, b, X and $P^2$ are as defined herein.

In one particular embodiment, the invention relates to processes for preparing intermediates useful for preparing (2S,4R)-5-biphenyl-4-yl-2-hydroxymethyl-2-methyl-4-[(1H-[1,2,3]triazole-4-carbonyl)-amino]-pentanoic acid 5-methyl-2-oxo-[1,3]dioxol-4-ylmethyl ester and tautomers thereof.

One aspect of the invention relates to a process for preparing a compound of formula I:

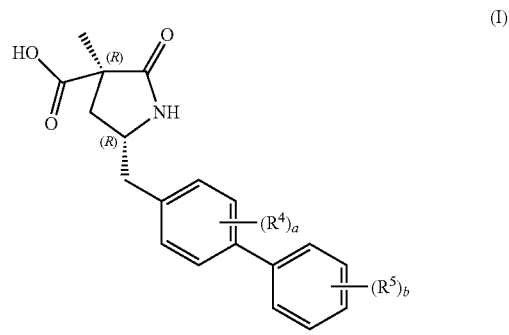

or a salt thereof, where $R^4$, $R^5$, a, and b are as defined herein; the process comprising the step of reslurrying a compound of formula (1):

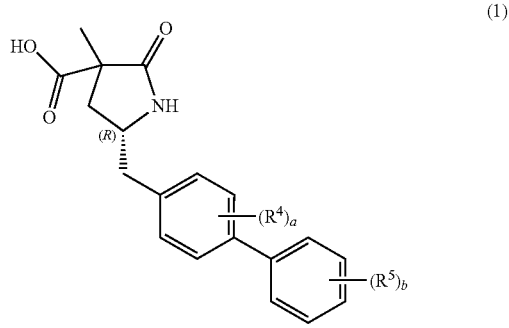

in an ether solvent to form a compound of formula I or a salt thereof.

Another aspect of the invention relates to a process for preparing a compound of formula IIa:

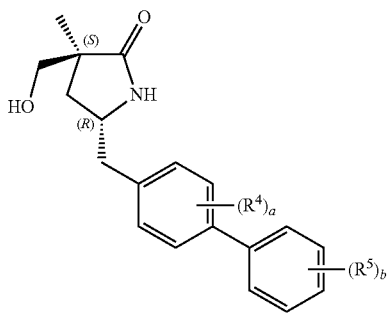

(IIa)

or a salt thereof, where $R^4$, $R^5$, a, and b are as defined herein; the process comprising the steps of (a) activation of the carboxyl group of a compound of formula I:

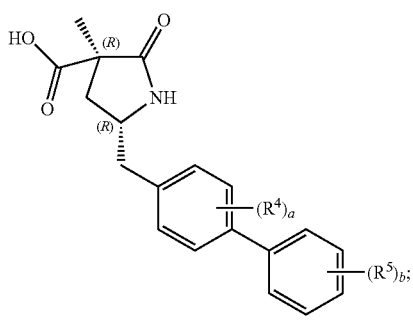

(I)

and (b) reacting the resulting product with a reducing agent to form a compound of formula IIa or a salt thereof.

Another aspect of the invention relates to intermediates used in the processes of the invention. In one such aspect of the invention, the intermediate has formula (II):

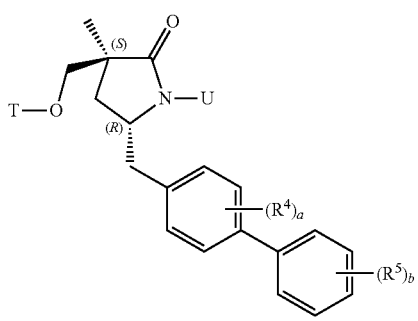

(II)

or a salt thereof, where $R^4$, $R^5$, a, b, T and U are as defined herein.

In another aspect of the invention, the intermediate has formula (III):

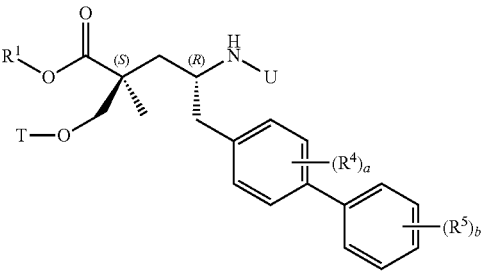

(III)

or a salt thereof, where $R^1$, $R^4$, $R^5$, a, b, T and U are as defined herein.

DETAILED DESCRIPTION OF THE INVENTION

The invention relates to processes for preparing compounds of formula IV:

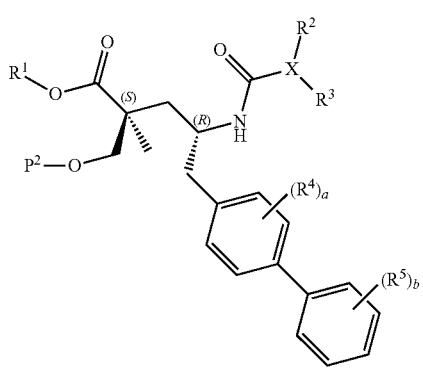

(IV)

or a tautomer or salt thereof. The $R^1$ moiety is selected from:
H;
—$C_{1-8}$alkyl, e.g., —$CH_3$, —$CH_2CH_3$, —$(CH_2)_2CH_3$, —$CH(CH_3)_2$, —$CH_2CH(CH_3)_2$, —$(CH_2)_3CH_3$, —$(CH_2)_4CH_3$, —$(CH_2)_2CH(CH_3)_2$, —$(CH_2)_5CH_3$, and —$(CH_2)_6CH_3$;
—$C_{1-3}$alkylene-$C_{6-10}$aryl, e.g., benzyl;
—$[(CH_2)_2O]_{1-3}CH_3$, e.g., —$(CH_2)_2OCH_3$ and —$[(CH_2)_2O]_2CH_3$;
—$C_{1-6}$alkylene-OC(O)$R^{10}$, e.g., —$CH_2OC(O)CH_3$, —$CH_2OC(O)CH_2CH_3$, —$CH_2OC(O)(CH_2)_2CH_3$, —$CH_2CH(CH_3)OC(O)CH_2CH_3$, —$CH_2OC(O)OCH_3$, —$CH_2OC(O)OCH_2CH_3$, —$CH(CH_3)OC(O)OCH_2CH_3$, —$CH(CH_3)OC(O)O$—$CH(CH_3)_2$, —$CH_2OC(O)O$-cyclopropyl, —$CH(CH_3)$—$OC(O)$—$O$-cyclohexyl, —$CH_2OC(O)$O-cyclopentyl, —$CH_2OC(O)$—$CH[CH(CH_3)_2]$—$NH_2$, and —$CH_2OC(O)$—$CH[CH(CH_3)_2]$—$NHC(O)OCH_3$;
—$C_{1-6}$alkylene-$NR^{11}R^{12}$, e.g., —$(CH_2)_2$—$N(CH_3)_2$,

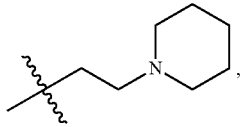

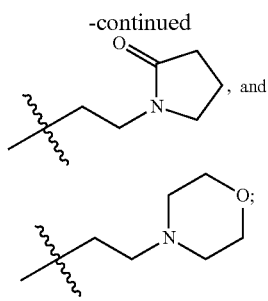, and

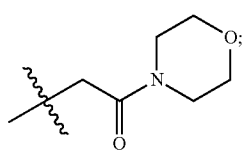 [SMILES: *CC(=O)N1CCOCC1]

—$C_{1-6}$alkylene-C(O)$R^{13}$, e.g., —$CH_2$C(O)O$CH_3$, —$CH_2$C(O)O-benzyl, —$CH_2$C(O)—N($CH_3$)$_2$, and

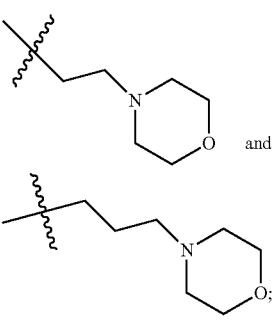

—$C_{0-6}$alkylenemorpholinyl, e.g., —($CH_2$)$_2$-morpholinyl and —($CH_2$)$_3$-morpholinyl:

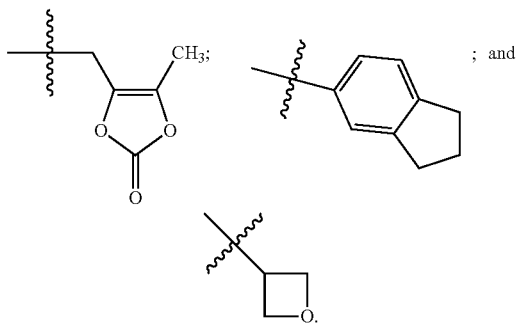

—$C_{1-6}$alkylene-SO$_2$—$C_{1-6}$alkyl, e.g., —($CH_2$)$_2$SO$_2$CH$_3$;

The $R^{10}$ moiety is selected from:
 —$C_{1-6}$alkyl, e.g., —$CH_3$ and —$CH_2CH_3$;
 —O—$C_{1-6}$alkyl e.g., —$OCH_3$, —O—$CH_2CH_3$, and —O—CH($CH_3$)$_2$;
 —O—$C_{3-7}$cycloalkyl, e.g., —O-cyclopropyl, —O-cyclohexyl, and —O-cyclopentyl;
 —CH[CH($CH_3$)$_2$]—NH$_2$; and
 —CH[CH($CH_3$)$_2$]—NHC(O)O—$C_{1-6}$alkyl.

The $R^{11}$ and $R^{12}$ moieties are —$C_{1-6}$alkyl (e.g., $CH_3$) or are taken together as —($CH_2$)$_{3-6}$—, —C(O)—($CH_2$)$_3$—, or —($CH_2$)$_2$O($CH_2$)$_2$—, for example to form a group such as:

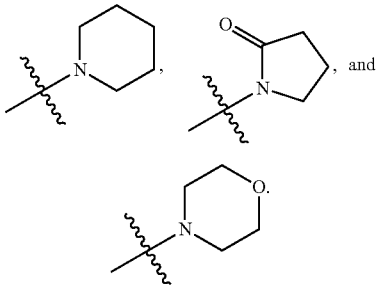

The $R^{13}$ moiety is selected from —O—$C_{1-6}$alkyl, e.g., —$OCH_3$, —O-benzyl, and —NR$^{11}$R$^{12}$, e.g., —N($CH_3$)$_2$, and

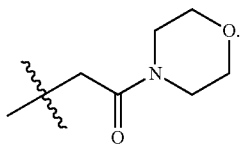 [SMILES: *CC(=O)N1CCOCC1]

In addition, each alkyl group in $R^1$ is optionally substituted with 1 to 8 fluoro atoms. For example, when $R^1$ is —$C_{1-8}$alkyl, $R^1$ can also be a group such as —CH($CH_3$)CF$_3$, —$CH_2CF_2CF_3$, —CH(CF$_3$)$_2$, —($CH_2$)$_2$CF$_3$, —CH(CH$_2$F)$_2$, —C(CF$_3$)$_2$CH$_3$, and —CH(CH$_3$)CF$_2$CF$_3$.

The "X" moiety is a heteroaryl selected from pyrazole, imidazole, triazole, benzotriazole, tetrazole, oxazole, isoxazole, thiazole, pyrimidine, pyridazine, benzimidazole, pyran, and pyridyltriazole, and the point of attachment is at any available carbon or nitrogen ring atom. Note that in some embodiments, $R^2$ may be absent. When present, $R^2$ is on any available carbon atom. $R^3$ is on any available carbon atom or nitrogen atom.

Pyrazole rings include:

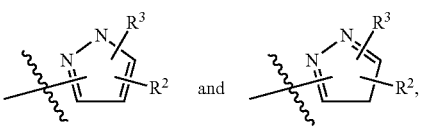

specific examples of which include:

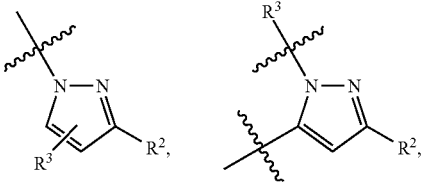

-continued
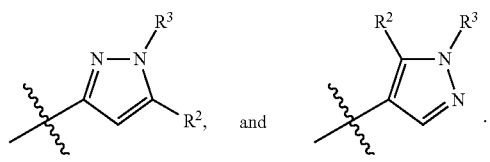 and 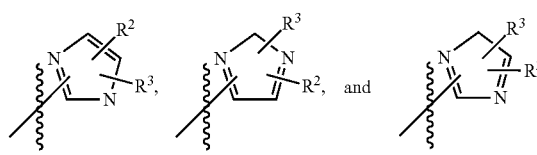.
Imidazole rings include:
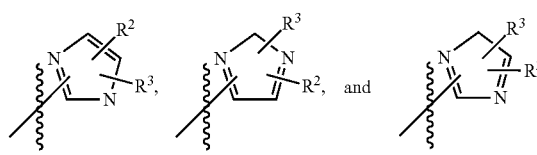
specific examples of which include:
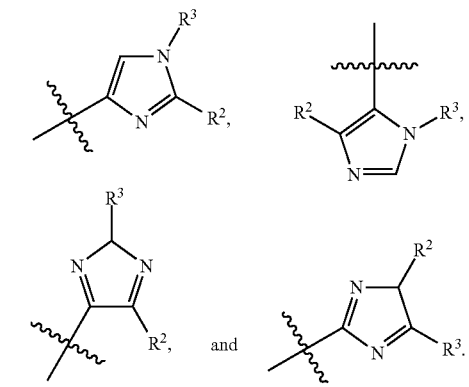
Triazole rings include 1,2,3-triazoles such as:
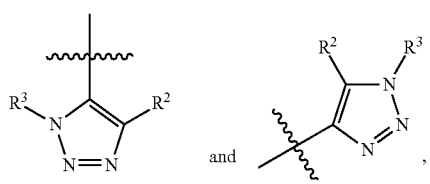
and
as well as 1,2,4-triazoles such as:
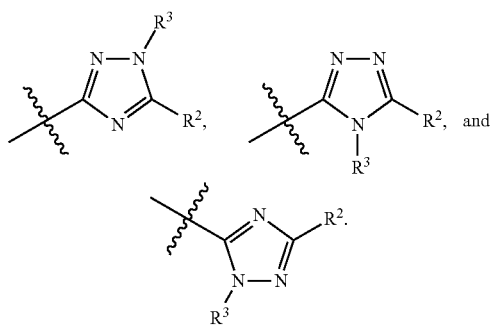
Benzotriazole rings include:
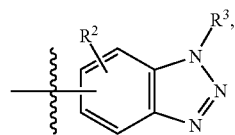
specific examples of which include:
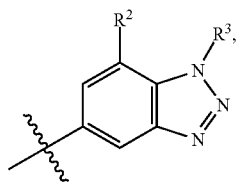
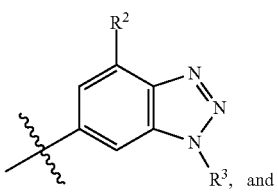, and
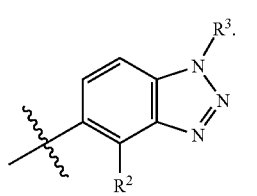.
Tetrazole rings include:
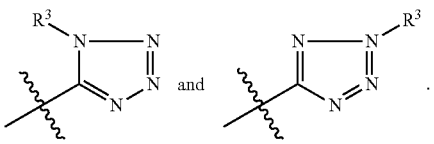
Oxazole rings include:
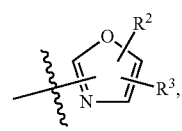,
specific examples of which include:
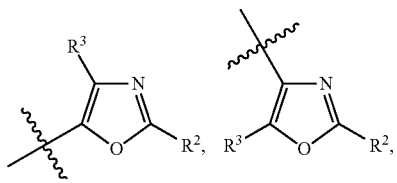

-continued
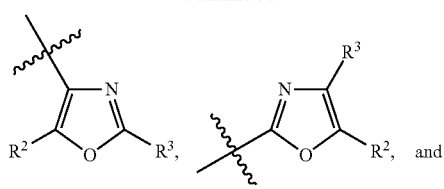
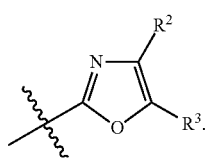
Isoxazole rings include:
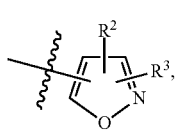
specific examples of which include:
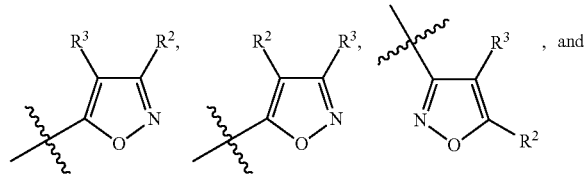
Thiazole rings include:
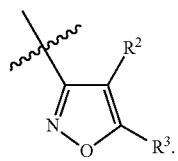
specific examples of which include:
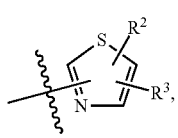
-continued
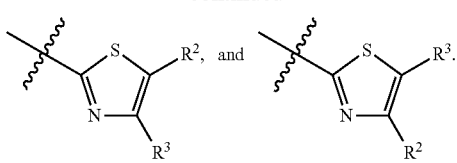
Pyrimidine rings include:
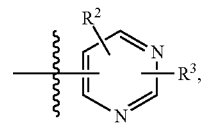
specific examples of which include:
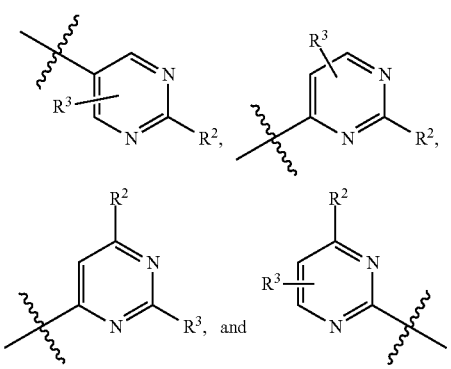
Pyridazine rings include:
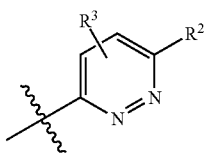
Benzimidazole rings include:
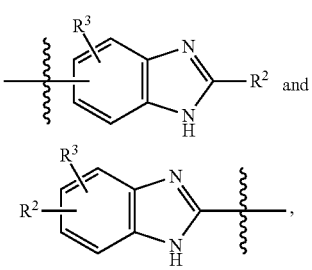

specific examples of which include:

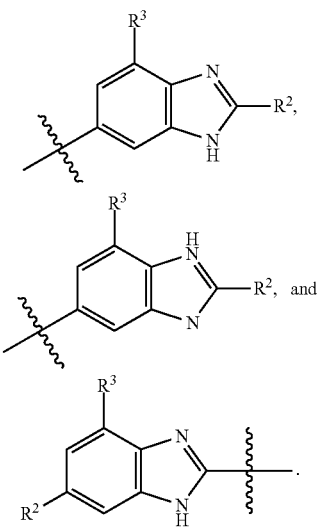

Pyran rings include:

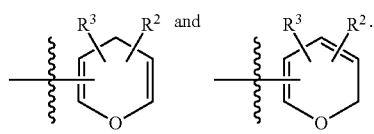

Pyridyltriazole rings include:

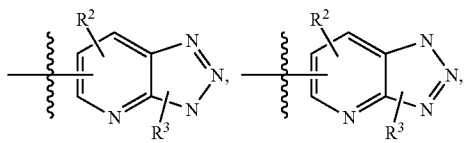

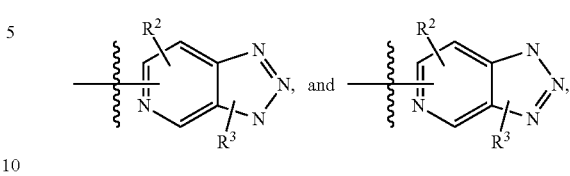

specific examples of which include:

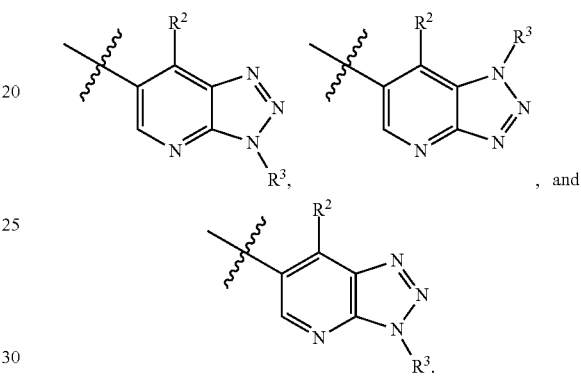

It is understood that some heteroaryl rings can exist in a tautomeric form, and that such tautomeric forms are part of the invention and are encompassed by the term "heteroaryl." Therefore, if a compound is depicted with X being one particular heteroaryl ring, it is understood that the compound can also exist in a tautomeric form and vice versa, and that both forms are covered by the invention.

| X | exemplary ring | exemplary tautomer(s) |
|---|---|---|
| pyrazole | | |
| imidazole | | |
| triazole | | |

| X | exemplary ring | exemplary tautomer(s) |
|---|---|---|
| oxazole | | |
| thiazole | | |
| pyridazine | | |

The $R^2$ moiety can be absent. When present, $R^2$ is attached to a carbon atom in the "X" group, and is selected from:

H;

halo, e.g., chloro and fluoro;

—$C_{0-5}$alkylene-OH, e.g., —OH, —$CH_2$OH, —CH(OH)$CH_3$, and —$C(CH_3)_2$—OH;

—$C_{1-6}$alkyl, e.g., —$CH_3$, —$(CH_2)_2CH_3$, —$CH(CH_3)_2$, and —$(CH_2)_3$—$CH_3$;

—$C_{3-7}$cycloalkyl, e.g., cyclopropyl and cyclohexyl;

—$C_{0-2}$alkylene-O—$C_{1-6}$alkyl, e.g., —$OCH_3$, —$OCH_2CH_3$, —$CH_2$—$OCH_3$, and —$(CH_2)_2$—$OCH_3$;

—$C(O)C_{1-6}$ alkyl, e.g., —$C(O)CH_3$;

—$C_{0-1}$alkylene-COOH, e.g., —COOH and —$CH_2$—COOH;

—$C(O)NR^{20}R^{21}$, e.g., —$C(O)NH_2$, —$C(O)NHCH_3$, —$C(O)N(CH_3)_2$, —$C(O)NH$—$(CH_2)_2CH_3$, —$C(O)NH$—$(CH_2)_2$—OH, —$C(O)NH$-cyclopropyl, —$C(O)N(CH_3)$—$CH_2CH(CH_3)_2$, and —$C(O)N(CH_3)[(CH_2)_2OCH_3]$;

—NHC(O)-phenylene-$OCH_3$, e.g., —NHC(O)-2-methoxyphenyl;

=O;

phenyl optionally substituted with one or two groups independently selected from halo, —OH, and —$OCH_3$, e.g., phenyl, 2-chlorophenyl, 2-fluorophenyl, 2-hydroxyphenyl, 2-methoxyphenyl, 3-chlorophenyl, 3-fluorophenyl, 3-methoxyphenyl, 4-chlorophenyl, 4-fluorophenyl, 4-methoxyphenyl, 2,5-dimethoxyphenyl, 2,4-dichlorophenyl, 2-methoxy, 5-fluorophenyl, and 3,4-dichlorophenyl;

pyridinyl; and pyrazinyl.

The $R^{20}$ moiety is H or —$C_{1-6}$alkyl (e.g., —$CH_3$ and —$(CH_2)_2CH_3$). The $R^{21}$ moiety is selected from H, —$C_{1-6}$alkyl (e.g., —$CH_3$ and —$(CH_2)_2CH_3$), —$(CH_2)_2$OH, —$(CH_2)_2OCH_3$, —$(CH_2)_2SO_2NH_2$, and —$C_{0-1}$alkylene-$C_{3-7}$cycloalkyl (e.g., cyclopropyl and —$CH_2$-cyclopropyl). $R^{20}$ and $R^{21}$ may also be taken together to form a saturated or partially unsaturated —$C_{3-5}$heterocycle optionally substituted with halo or —OH, and optionally containing an oxygen atom in the ring. Saturated —$C_{3-5}$heterocycles include azetidine, pyrrolidine, piperidine and morpholine, such that exemplary $R^2$ groups include:

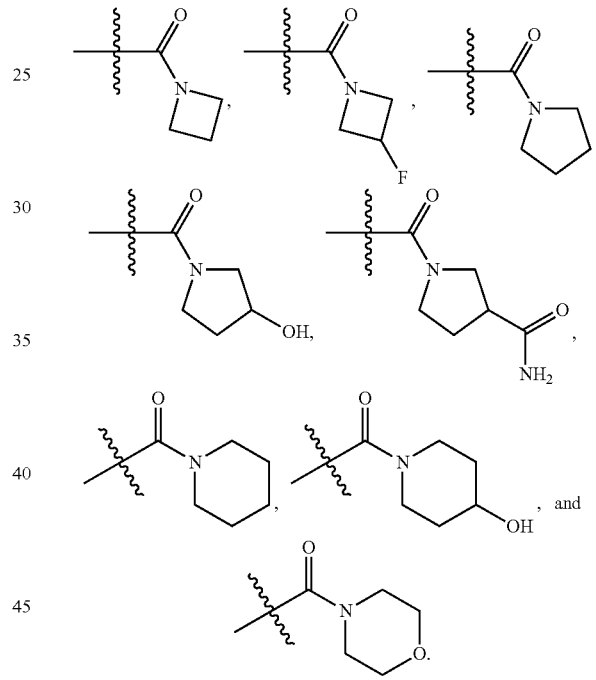

Partially unsaturated —$C_{3-5}$heterocycles include 2,5-dihydro-1H-pyrrole, such that exemplary $R^2$ groups include:

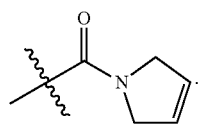 [SMILES: *C(=O)N1CC=CC1]

In addition, each alkyl group in $R^2$ is optionally substituted with 1 to 8 fluoro atoms. For example, when $R^2$ is —$C_{1-6}$alkyl, $R^2$ can also be a group such as —$CH(CH_3)CF_3$, —$CH_2CF_2CF_3$, —$CH(CF_3)_2$, —$(CH_2)_2CF_3$, —$CH(CH_2F)_2$, —$C(CF_3)_2CH_3$, and —$CH(CH_3)CF_2CF_3$.

The $R^3$ moiety s attached to a carbon or nitrogen atom in the "X" group, and is selected from:

H;
—OH;
—C$_{1-6}$alkyl, e.g., —CH$_3$;
—C$_{1-2}$alkylene-COOH, e.g., —CH$_2$COOH and —(CH$_2$)$_2$—COOH;
—CH$_2$OC(O)CH(R$^{30}$)NH$_2$, e.g., —CH$_2$OC(O)CH[CH(CH$_3$)$_2$]NH$_2$;
—CH[CH(CH$_3$)$_2$]—NHC(O)O—C$_{1-6}$alkyl;
pyridinyl; and
phenyl or benzyl optionally substituted with one or more groups selected from halo and —OCH$_3$ (e.g., 4-chlorophenyl, 3-methoxyphenyl, 2,4-dichlorophenyl, 3,4-dichlorophenyl, 2-chloro, 5-fluorophenyl, 4-chlorophenyl, 2,6-difluoro, 4-chlorophenyl, 2-chlorobenzyl, 3-chlorobenzyl, 4-chlorobenzyl, 3-methoxybenzyl, 2-chloro, 5-fluorobenzyl, 3-chloro, 5-fluorobenzyl, 2-fluoro, 4-chlorobenzyl, 3-chloro, 4-fluorobenzyl, 2,6-difluoro, 3-chlorobenzyl, 2,6-difluoro, 4-chlorobenzyl, and 2,3,5,6-tetrafluoro, 4-methoxy benzyl).

The R$^{30}$ moiety is selected from H, —CH(CH$_3$)$_2$, phenyl, and benzyl. In addition, when R$^3$ is attached to nitrogen atom, R$^3$ can be P$^4$, where P$^4$ is an amino protecting group. In addition, each alkyl group in R$^3$ is optionally substituted with 1 to 8 fluoro atoms. For example, when R$^3$ is —C$_{1-6}$alkyl, R$^3$ can also be a group such as —CH(CH$_3$)CF$_3$, —CH$_2$CF$_2$CF$_3$, —CH(CF$_3$)$_2$, —(CH$_2$)$_2$CF$_3$, —CH(CH$_2$F)$_2$, —C(CF$_3$)$_2$CH$_3$, and —CH(CH$_3$)CF$_2$CF$_3$.

The numbering for the R$^4$ and R$^5$ groups is as follows:

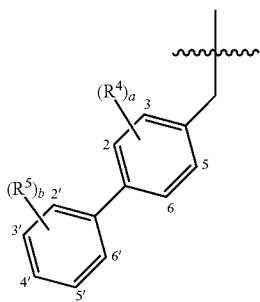

The integer "a" is 0 or 1. The R$^4$ moiety, when present, is selected from halo, —CH$_3$, —CF$_3$, and —CN. In one embodiment, a is 0. In another embodiment, a is 1, and R$^4$ is halo, such as 3-chloro or 3-fluoro. The integer "b" is 0 or an integer from 1 to 3. The R$^5$ moiety, when present, is independently selected from halo, —OH, —CH$_3$, —OCH$_3$, and —CF$_3$. In one embodiment, b is 0. In another embodiment, b is 1 and R$^5$ is selected from Cl, F, —OH, —CH$_3$, —OCH$_3$, and —CF$_3$, such 2'-chloro, 3'-chloro, 2'-fluoro, 3'-fluoro, 2'-hydroxy, 3'-hydroxy, 3'-methyl, 2'-methoxy, or 3'-trifluoromethyl. In another embodiment, b is 1 and R$^5$ is halo, —CH$_3$, or —OCH$_3$, such 3'-chloro, 3'-methyl, or 2'-methoxy. In one embodiment, b is 2 and R$^5$ is 2'-fluoro-5'-chloro, 2',5'-dichloro, 2',5'-difluoro, 2'-methyl-5'-chloro, 3'-fluoro-5'-chloro, 3'-hydroxy-5'-chloro, 3',5'-dichloro, 3',5'-difluoro, 2'-methoxy-5'-chloro, 2'-methoxy-5'-fluoro, 2'-hydroxy-5'-fluoro, 2'-fluoro-3'-chloro, 2'-hydroxy-5'-chloro, or 2'-hydroxy-3'-chloro; and in another embodiment, b is 2 and each R$^5$ is independently halo, for example, 2'-fluoro-5'-chloro and 2',5'-dichloro. In another embodiment, b is 3 and each R$^5$ is independently halo or —CH$_3$, such as 2'-methyl-3',5'-dichloro or 2'-fluoro-3'-methyl-5'-chloro. In yet another embodiment, a is 1 and b is 1 and R$^4$ and R$^5$ are independently halo, for example, 3-chloro and 3' chloro.

DEFINITIONS

When describing the compounds and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The compounds described herein have typically been named using the AutoNom feature of the commercially-available MDL® ISIS/Draw software (Symyx, Santa Clara, Calif.).

As used herein, the phrase "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "alkyl" means a monovalent saturated hydrocarbon group which may be linear or branched. Unless otherwise defined, such alkyl groups typically contain from 1 to 10 carbon atoms and include, for example, —C$_{1-4}$alkyl, —C$_{1-5}$alkyl, —C$_{2-5}$alkyl, —C$_{1-6}$alkyl, —C$_{1-8}$alkyl, and —C$_{1-10}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—C$_{1-6}$alkyl" means an alkyl group having from 1 to 6 carbon atoms, and the term "—C$_{3-7}$cycloalkyl" means a cycloalkyl group having from 3 to 7 carbon atoms, respectively, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, —C$_{0-1}$alkylene-, —C$_{0-6}$alkylene-, —C$_{1-3}$alkylene-, and —C$_{1-6}$alkylene-. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —C$_{0-1}$alkylene-, such terms are intended to include the absence of carbon atoms, that is, the alkylene group is not present except for a covalent bond attaching the groups separated by the alkylene term.

The term "aryl" means a monovalent aromatic hydrocarbon having a single ring (i.e., phenyl) or one or more fused rings. Fused ring systems include those that are fully unsaturated (e.g., naphthalene) as well as those that are partially unsaturated (e.g., 1,2,3,4-tetrahydronaphthalene). Unless otherwise defined, such aryl groups typically contain from 6 to 10 carbon ring atoms and include, for example, —C$_{6-10}$aryl. Representative aryl groups include, by way of example, phenyl and naphthalene-1-yl, naphthalene-2-yl, and the like.

The term "cycloalkyl" means a monovalent saturated carbocyclic hydrocarbon group. Unless otherwise defined, such cycloalkyl groups typically contain from 3 to 10 carbon atoms and include, for example, —C$_{3-5}$cycloalkyl, —C$_{3-6}$cycloalkyl and —C$_{3-7}$cycloalkyl. Representative cycloalkyl groups include, by way of example, cyclopropyl, cyclobutyl, cyclopentyl, cyclohexyl and the like.

The term "halo" means fluoro, chloro, bromo and iodo.

The term "heterocycle" is intended to include monovalent unsaturated (aromatic) heterocycles having a single ring or two fused rings as well as monovalent saturated and partially unsaturated groups having a single ring or multiple condensed rings. The heterocycle ring can contain from 3 to 15 total ring atoms, of which 1 to 14 are ring carbon atoms, and 1 to 4 are ring heteroatoms selected from nitrogen, oxygen or sulfur. Typically, however, the heterocycle ring contains from 3 to 10 total atoms, of which 1 to 9 are ring carbon atoms, and 1 to 4 are ring heteroatoms. The point of attachment is at any available carbon or nitrogen ring atom. Exemplary heterocycles include, for example, —C$_{1-7}$heterocycle, —C$_{3-5}$heterocycle, —C$_{2-6}$heterocycle, —C$_{3-12}$heterocycle, —C$_{5-9}$heterocycle, —C$_{1-9}$heterocycle, —C$_{1-11}$heterocycle, and —C$_{1-14}$heterocyle.

Monovalent unsaturated heterocycles are also commonly referred to as "heteroaryl" groups. Unless otherwise defined, heteroaryl groups typically contain from 5 to 10 total ring atoms, of which 1 to 9 are ring carbon atoms, and 1 to 4 are ring heteroatoms, and include, for example, —C$_{1-9}$heteroaryl and —C$_{5-9}$heteroaryl. Representative heteroaryl groups include, by way of example, pyrrole (e.g., 3-pyrrolyl and 2H-pyrrol-3-yl), imidazole (e.g., 2-imidazolyl), furan (e.g., 2-furyl and 3-furyl), thiophene (e.g., 2-thienyl), triazole (e.g., 1,2,3-triazolyl and 1,2,4-triazolyl), pyrazole (e.g., 1H-pyrazol-3-yl), oxazole (e.g., 2-oxazolyl), isoxazole (e.g., 3-isoxazolyl), thiazole (e.g., 2-thiazolyl and 4-thiazolyl), and isothiazole (e.g., 3-isothiazolyl), pyridine (e.g., 2-pyridyl, 3-pyridyl, and 4-pyridyl), pyridylimidazole, pyridyltriazole, pyrazine, pyridazine (e.g., 3-pyridazinyl), pyrimidine (e.g., 2-pyrimidinyl), tetrazole, triazine (e.g., 1,3,5-triazinyl), indolyle (e.g., 1H-indol-2-yl, 1H-indol-4-yl and 1H-indol-5-yl), benzofuran (e.g., benzofuran-5-yl), benzothiophene (e.g., benzo[b]thien-2-yl and benzo[b]thien-5-yl), benzimidazole, benzoxazole, benzothiazole, benzotriazole, quinoline (e.g., 2-quinolyl), isoquinoline, quinazoline, quinoxaline and the like.

Monovalent saturated heterocycles typically contain from 3 to 10 total ring atoms, of which 2 to 9 are ring carbon atoms, and 1 to 4 are ring heteroatoms, and include, for example —C$_{3-5}$heterocycle. Representative monovalent saturated heterocycles include, by way of example, monovalent species of pyrrolidine, imidazolidine, pyrazolidine, piperidine, 1,4-dioxane, morpholine, thiomorpholine, piperazine, 3-pyrroline and the like. In some instances, moieties may be described as being taken together to form a saturated —C$_{3-5}$heterocycle optionally containing an oxygen atom in the ring. Such groups include:

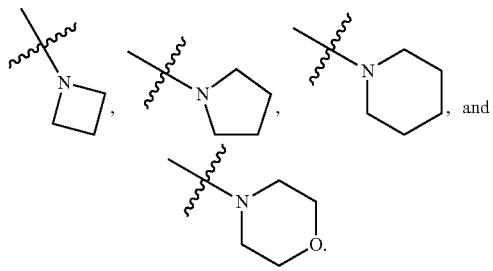

Monovalent partially unsaturated heterocycles typically contain from 3 to 10 total ring atoms, of which 2 to 11 are ring carbon atoms, and 1 to 3 are ring heteroatoms, and include, for example —C$_{3-5}$heterocycle and —C$_{2-12}$heterocycle. Representative monovalent partially unsaturated heterocycles include, by way of example, pyran, benzopyran, benzodioxole (e.g., benzo[1,3]dioxol-5-yl), tetrahydropyridazine, 2,5-dihydro-1H-pyrrole, dihydroimidazole, dihydrotriazole, dihydrooxazole, dihydroisoxazole, dihydrothiazole, dihydroisothiazole, dihydrooxadiazole, dihydrothiadiazole, tetrahydropyridazine, hexahydropyrroloquinoxaline, and dihydrooxadiazabenzo[e]azulene. In some instances, moieties may be described as being taken together to form a partially unsaturated —C$_{3-5}$heterocycle. Such groups include:

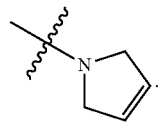

The term "optionally substituted" means that group in question may be unsubstituted or it may be substituted one or several times, such as 1 to 3 times, or 1 to 5 times, or 1 to 8 times. For example, a phenyl group that is "optionally substituted" with halo atoms, may be unsubstituted, or it may contain 1, 2, 3, 4, or 5 halo atoms; and an alkyl group that is "optionally substituted" with fluoro atoms may be unsubstituted, or it may contain 1, 2, 3, 4, 5, 6, 7, or 8 fluoro atoms. Similarly, a group that is "optionally substituted" with one or two —C$_{1-6}$alkyl groups, may be unsubstituted, or it may contain one or two —C$_{1-6}$alkyl groups.

The term "protecting group" or "blocking group" refers to a group which, when covalently attached to a functional group such as an amino or alcohol group, prevents the functional group from undergoing undesired reactions but which permits the functional group to be regenerated (i.e., deprotected or unblocked) upon treatment of the protecting group with a suitable reagent.

The term "salt" when used in conjunction with a compound means a salt of the compound derived from an inorganic or organic base or from an inorganic or organic acid. Salts derived from inorganic bases include aluminum, ammonium, calcium, copper, ferric, ferrous, lithium, magnesium, manganic, manganous, potassium, sodium, zinc, and the like. Particularly preferred are ammonium, calcium, magnesium, potassium and sodium salts. Salts derived from organic bases include salts of primary, secondary and tertiary amines, including substituted amines, cyclic amines, naturally-occurring amines, and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. Salts derived from acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic, and the like. Particularly preferred are citric, hydrobromic, hydrochloric, maleic, phosphoric, sulfuric and tartaric acids. In addition, when a compound contains both a basic moiety, such as an amine, and an acidic moiety such as a carboxylic acid, zwitterions may be formed and are included within the term "salt" as used herein. The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered by the invention are not required to be pharmaceutically acceptable salts, such as salts of intermediate compounds that are not intended for administration to a patient.

Process Conditions

Suitable inert diluents for use in the process of the invention include, by way of illustration and not limitation, organic diluents such as acetic acid, tetrahydrofuran (THF), acetonitrile (MeCN), N,N-dimethylformamide (DMF), N,N-dimethylacetamide, N-methylpyrrolidinone, dimethyl sulfoxide (DMSO), toluene, dichloromethane (DCM), acetone, ethyl acetate, isopropyl acetate, methyl t-butyl ether, chloroform ($CHCl_3$), carbon tetrachloride ($CCl_4$), 1,4-dioxane, methanol, ethanol, propanol, isopropanol, butanol, ethylene glycol, and the like. Aqueous diluents may also be used, and include water as well as basic and acidic aqueous diluents. Combinations of any of the foregoing diluents are also contemplated.

Representative amino protecting groups (depicted herein as $P^1$, $P^3$, and $P^4$) include, but are not limited to:
  base labile N-α-amino acid protecting groups removed by bases, such as 9-fluorenylmethoxycarbonyl (Fmoc) and benzoyl (Bz);
  protecting groups removed by acids, such as t-butoxycarbonyl (Boc), β-trimethylsilylethyloxycarbonyl (TEOC), t-amyloxycarbonyl (Aoc), adamantyl-oxycarbonyl (Adoc), 1-methylcyclobutyloxycarbonyl (Mcb), 2-(p-biphenylyl)propyl-2-oxycarbonyl (Bpoc), 2-(p-phenylazophenyl)propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), 2-furanmethyloxycarbonyl (Foc), p-methoxybenzyl carbonyl (Moz), o-nitrophenylsulfenyl (Nps), tosyl (Ts), trityl, triphenylmethyl (Tr), and silyl ethers (e.g., trimethylsilyl (TMS), t-butyldimethylsilyl (TBS), tri-iso-propylsilyloxymethyl (TOM), and triisopropylsilyl (TIPS) ethers);
  protecting groups removed by hydrogenolysis such as dithiasuccinoyl (Dts), benzyl (Bn), Cbz, p-methoxybenzyl (PMB), 3,4-dimethoxybenzyl (DMPM), and Moz;
  protecting groups removed by nucleophiles, such as 2-(t-butylsulfonyl)-2-propenyloxycarbonyl (Bspoc), benzothiophene sulfone-2-methoxycarbonyl (Bsmoc), and Nps; and
  protecting groups derived from carboxylic acids, such as formyl, acetyl, and trifluoroacetyl, which are removed by acids, bases, or nucleophiles.

In one embodiment, the amino protecting group is selected from: acetyl, adamantyl-oxycarbonyl, t-amyloxycarbonyl, benzothiophene sulfone-2-methoxycarbonyl, benzoyl, benzyl, benzyloxycarbonyl, 2-(p-biphenylyl)propyl-2-oxycarbonyl, t-butoxycarbonyl, 2-(t-butylsulfonyl)-2-propenyloxycarbonyl, 3,4-dimethoxybenzyl, 2,2-dimethyl-3,5-dimethyloxybenzyloxycarbonyl, dithiasuccinoyl, formyl, 9-fluorenylmethoxycarbonyl, 2-furanmethyloxycarbonyl, p-methoxybenzyl, p-methoxybenzyl carbonyl, 1-methylcyclobutyloxycarbonyl, o-nitrophenylsulfenyl, 2-phenylpropyl-2-oxycarbonyl, 2-(p-phenylazophenyl)propyl-2-oxycarbonyl, silyl ethers, tosyl, trifluoroacetyl, β-trimethylsilylethyloxycarbonyl, triphenylmethyl, and trityl.

Standard protection and deprotection techniques and reagents are used to add and later remove an amino protecting group. For example, the amino protecting group Boc is added with the amino protecting reagent di-t-butyldicarbonate and is removed with an acid such as HCl; and so forth. Other representative techniques and reagents are described, for example, in T. W. Greene and G. M. Wuts, *Protecting Groups in Organic Synthesis*, Fourth Edition, Wiley, New York, 2006.

Representative alcohol protecting groups (depicted herein as $P^2$) include, but are not limited to:
  protecting groups removed by acids, such as acetyl (Ac), benzoyl (Bz), β-methoxyethoxymethyl ether (MEM), p-methoxybenzyl ether (PMB), methylthiomethyl ether, pivaloyl (Piv), tetrahydropyranyl (THP), trityl or triphenylmethyl (Tr), and silyl ethers (e.g., trimethylsilyl (TMS), t-butyldimethylsilyl (TBS), tri-iso-propylsilyloxymethyl (TOM), and triisopropylsilyl (TIPS) ethers);
  protecting groups removed by bases, such as Ac, Bz, and Piv;
  protecting groups removed by hydrogenolysis, such as benzyl (Bn), PMB, and Tr;
  protecting groups removed by oxidation, such as PMB; and
  protecting groups removed by fluoride ions (e.g., NaF, tetra-n-butylammonium fluoride, HF-Pyridine, or HF-triethylamine), such as silyl ethers.

In one embodiment, the alcohol protecting group is selected from acetyl, benzoyl, benzyl, p-methoxybenzyl ether, β-methoxyethoxymethyl ether, methylthiomethyl ether, pivaloyl, silyl ethers, tetrahydropyranyl, triphenylmethyl, and trityl.

Standard protection and deprotection techniques and reagents are used to add and later remove an alcohol protecting group. For example, the alcohol protecting group THP is added with the alcohol-protecting reagent dihydropyran and is removed with an acid such as HCl; the alcohol protecting group Tr is added with triphenylmethyl chloride and is removed with an acid such as HCl; and so forth. Other representative techniques and reagents are described, for example, in T. W. Greene and G. M. Wuts, *Protecting Groups in Organic Synthesis*, Fourth Edition, Wiley, New York, 2006.

There are numerous acids that are suitable for use in the process of the invention, and include, by way of illustration and not limitation, boric, carbonic, nitric ($HNO_3$), phosphoric ($H_3PO_4$), sulfamic and sulfuric acids (e.g., sulfuric acid, methanesulfonic acid, and p-toluenesulfonic acid), as well as hydrohalic acids such as hydrobromic (HBr), hydrochloric (HCl), hydrofluoric (HF), and hydroiodic (HI) acid.

There are numerous bases that are suitable for use in the process of the invention. Exemplary organic bases include, by way of illustration and not limitation: amines including primary alkylamines (e.g., methylamine, ethanolamine, the buffering agent tris, and the like), secondary alkylamines (e.g., dimethylamine, methylethanolamine, N,N-diisopropylethylamine, and the like), tertiary amines (e.g., trimethylamine, triethylamine, N-methylmorpholine, and the like); ammonia compounds such as ammonium hydroxide and hydrazine; alkali metal hydroxides such as lithium hydroxide, sodium hydroxide, sodium methoxide, potassium hydroxide, potassium t-butoxide, and the like; metal hydrides; and alkali metal carboxylate salts such as sodium acetate and the like. Exemplary inorganic bases, include, by way of illustration and not limitation: alkali metal carbonates such as lithium carbonate, potassium carbonate, cesium carbonate, sodium carbonate, sodium bicarbonate, and the like; other carbonates such as calcium carbonate and the like; alkali metal phosphates such as potassium phosphate and the like; and metal bis(trimethylsilyl)amide complexes such as sodium hexamethyldisilazide, lithium bis(trimethylsilyl)amide, and potassium bis(trimethylsilyl)amide.

Suitable inert diluents for use in these schemes include, by way of illustration and not limitation, tetrahydrofuran, acetonitrile, N,N-dimethylformamide, N,N-dimethylacetamide, dimethyl sulfoxide, toluene, dichloromethane, chloroform, carbon tetrachloride, 1,4-dioxane, methanol, ethanol, water, and the like.

Suitable ether solvents include, by way of illustration and not limitation, cyclopentyl methyl ether, di-t-butyl ether, diethyl ether, diglyme, diisopropyl ether, dimethoxyethane, dimethoxymethane, 1,4-dioxane, ethyl t-butyl ether, methoxyethane, methyl t-butyl ether, 2-methyltetrahydrofuran, morpholine, tetrahydrofuran, tetrahydropyran, and combinations thereof.

Suitable reducing agents include, by way of illustration and not limitation: hydride reagents such as lithium aluminum hydride ($LiAlH_4$), sodium borohydride ($NaBH_4$) and diborane; metals and organometallic reagents such as Grignard reagents, dialkylcopper lithium (lithium dialkylcuprate) reagents, and sodium, alkyl sodium and alkyl lithium.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), N,N,N',N'-tetramethyl-O-(7-azabenzotriazol-1-yl)uronium hexafluorophosphate (HATU), (2-(6-chloro-1H-benzotriazole-1-yl)-1,1,3,3-tetramethylaminium hexafluorophosphate) (HCTU), 1,3-dicyclohexylcarbodiimide (DCC), N-(3-dimethylaminopropyl)-N'-ethylcarbodiimide (EDCI), carbonyldiimidazole (CDI), 1-hydroxybenzotriazole (HOBt), and the like.

In some instances, the process steps were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, the process steps were conducted at room temperature and the temperature was actually measured and recorded. While optimum reaction conditions will typically vary depending on various reaction parameters such as the particular reactants, solvents and quantities used, those of ordinary skill in the art can readily determine suitable reaction conditions using routine optimization procedures.

Upon completion of any of the process steps, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, HCl); washing (for example, with aqueous $KHSO_4$, ethanol, heptanes, saturated aqueous NaCl, saturated aqueous $NaHCO_3$, saturated aqueous $NH_4Cl$, $Na_2CO_3$ (5%), $CHCl_3$ or 1M NaOH); distillation; drying (for example, over $MgSO_4$, over $Na_2SO_4$, under nitrogen, or under reduced pressure); precipitation; filtration; crystallizing (for example, from ethanol, heptanes or isopropyl acetate); being concentrated (for example, in vacuo); and/or purification.

Upon completion of any of the crystallization steps, the crystalline compound can be isolated from the reaction mixture by any conventional means such as precipitation, concentration, centrifugation, drying (for example, at room temperature), and the like.

Compounds of Formula I

The invention relates to processes for preparing compounds of formula I:

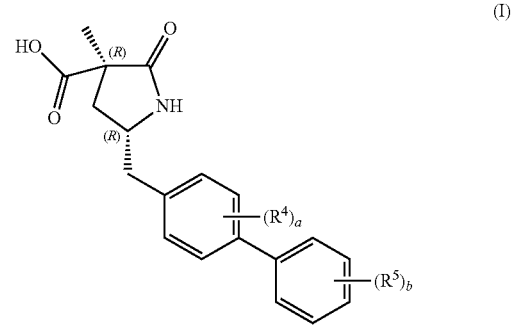

(I)

or a salt thereof; where a is 0 or 1; $R^4$ is selected from halo, —$CH_3$, —$CF_3$, and —CN; b is 0 or an integer from 1 to 3; and each $R^5$ is independently selected from halo, —OH, —$CH_3$, —$OCH_3$, and —$CF_3$. In one particular embodiment, a and b are 0.

The process for preparing a compound of formula I is a one step crystallization reaction:

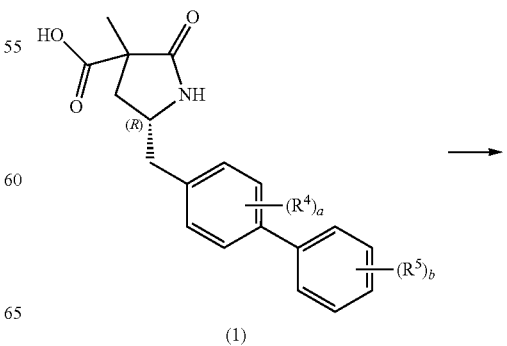

(1)

-continued

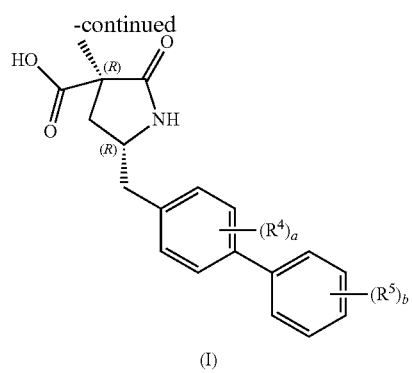

(I)

This reaction involves reslurrying Compound 1 to form a compound of formula I or a salt thereof. The reslurrying is conducted in an ether solvent or combination thereof. In one embodiment, the ether solvent is 2-methyltetrahydrofuran; and in another embodiment, the ether solvent is 2-methyltetrahydrofuran in combination with cyclopentyl methyl ether. In general, this process is conducted at room temperature.

This process provides a compound having ≥95% of the desired (R,R) diastereoisomer; and in one embodiment, ≥98% of the desired (R,R) diastereoisomer.

The starting material, Compound 1 is prepared by a one step reaction:

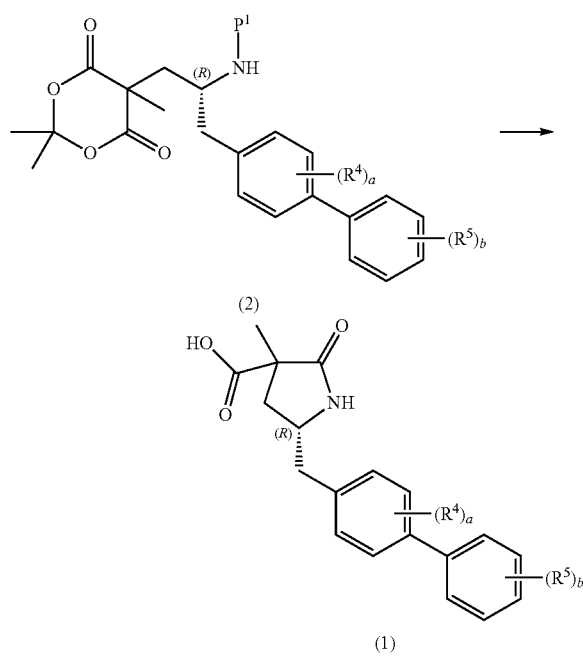

$P^1$ is an amino protecting group, and in one embodiment is t-butoxycarbonyl. This reaction involves acidic deprotection of Compound 2. Generally the deprotection occurs in an ether solvent and is conducted at room temperature. In one embodiment, acidic deprotection is accomplished using hydrochloric acid, for example, 3M HCl. In one embodiment, the ether solvent is cyclopentyl methyl ether. Generally, the product is obtained as a mixture of diastereoisomers.

Compound 2 can be prepared by conventional procedures using commercially available starting materials and conventional reagents.

Compounds of Formula II

The invention relates to compounds of formula II and processes for preparing them:

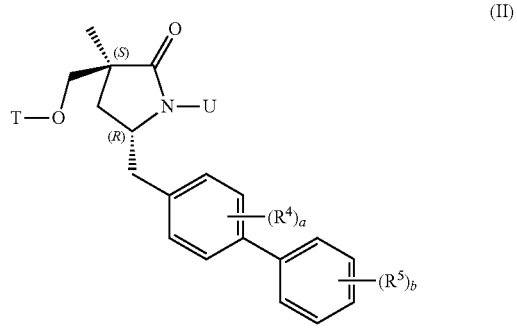

(II)

or a salt thereof. The integer a is 0 or 1, and $R^4$ is selected from halo, —$CH_3$, —$CF_3$, and —CN. In one particular embodiment, a is 0. The integer b is 0 or an integer from 1 to 3, and each $R^5$ is independently selected from halo, —OH, —$CH_3$, —$OCH_3$, and —$CF_3$. In one particular embodiment, b is 0.

T is H or $P^2$, where $P^2$ is an alcohol protecting group. In one particular embodiment, T is H or tetrahydropyran.

U is H or $P^3$, where $P^3$ is an amino protecting group. In one particular embodiment, U is H or t-butoxycarbonyl.

Exemplary embodiments include:
compounds of formula IIa: T is H; U is H; and a, b, $R^4$, and $R^5$ are as defined for compounds of formula II;
compounds of formula IIb: T is $P^2$; U is H; and a, b, $R^4$, and $R^5$ are as defined for compounds of formula II;
compounds of formula IIc: T is $P^2$; U is $P^3$; and a, b, $R^4$, and $R^5$ are as defined for compounds of formula II; and
compounds of formula IId: T is H; U is $P^3$; and a, b, $R^4$, and $R^5$ are as defined for compounds of formula II.

The process for preparing a compound of formula IIa is a two step process:

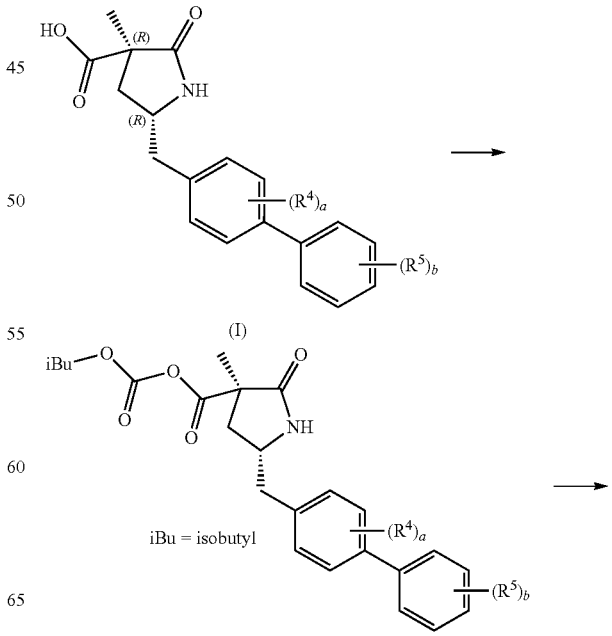

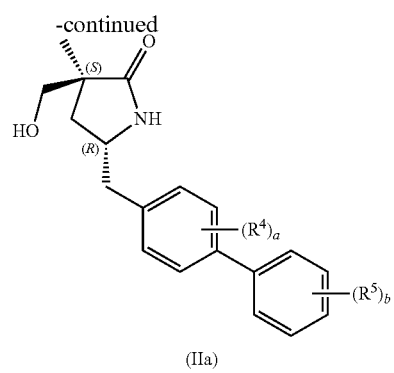

(IIa)

Step (a) involves activation of the carboxyl group of the compound of formula (I). generally this is done with isobutyl chloroformate in the presence of a tertiary amine base. In one embodiment the base is N-methylmorpholine. This step is typically conducted in a suitable inert diluent such as tetrahydrofuran, and is generally conducted at a temperature within the range of about –5 to 5° C. Step (b) is involves reacting the activated compound with a reducing agent. In one embodiment the reducing agent is sodium borohydride. This step is typically conducted in a suitable inert diluent such as water, and is generally conducted at a temperature within the range of about –5 to 5° C.

The process for preparing a compound of formula IIb involves protecting the alcohol on the compound of formula IIa:

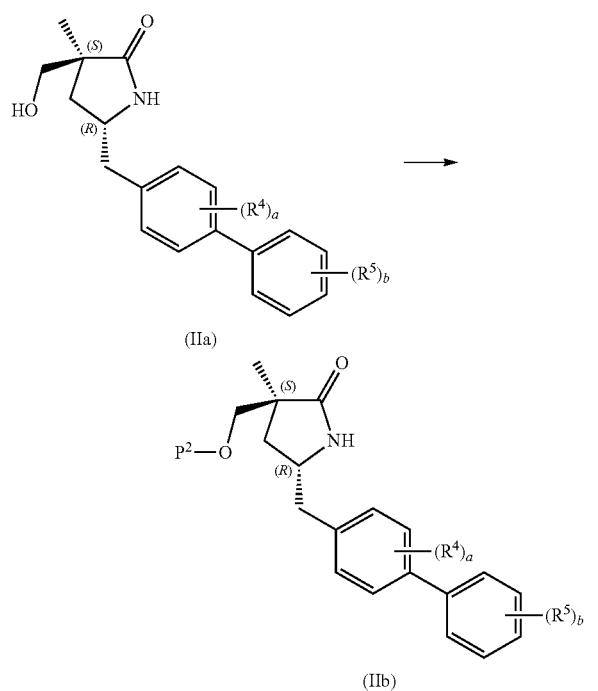

This reaction involves reacting a compound of formula IIa with an alcohol protecting reagent in the presence of an acid. In one embodiment, the alcohol protecting reagent is dihydropyran, resulting in $P^2$ being tetrahydropyranyl. A particularly suitable acid is p-toluenesulfonic acid. This step is typically conducted in a suitable inert diluent such as dichloromethane, and is generally conducted initially at a temperature within the range of about –5 to 5° C., then at about room temperature. In another embodiment, the compound of formula IIb is prepared as a crystalline material, by adding an inert diluent such as diisopropyl ether to the reaction mixture, and optionally adding seed crystals, followed by reslurrying, filtration, and drying The process for preparing a compound of formula IIc involves protecting the amine on the compound of formula IIb:

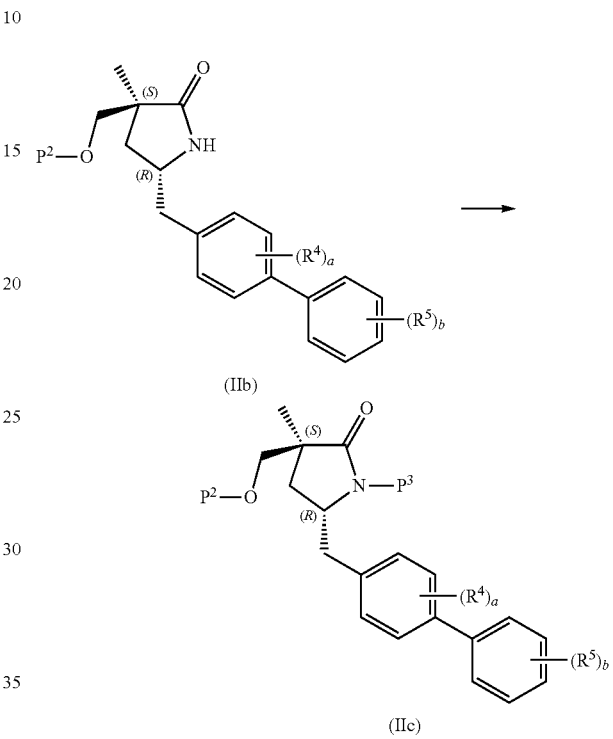

This reaction involves reacting a compound of formula IIb with an amino protecting reagent in the presence of a base. In one embodiment, the amino protecting reagent is di-t-butyl-dicarbonate, resulting in $P^3$ being t-butoxycarbonyl. A particularly suitable base is sodium hexamethyldisilazide. This step is typically conducted in a suitable inert diluent such as tetrahydrofuran, and is generally conducted at a temperature within the range of about –5 to 5° C. In one embodiment $P^2$ is tetrahydropyranyl. In another embodiment $P^3$ is t-butoxycarbonyl.

The process for preparing a compound of formula IId involves protecting the amine on the compound of formula IIa:

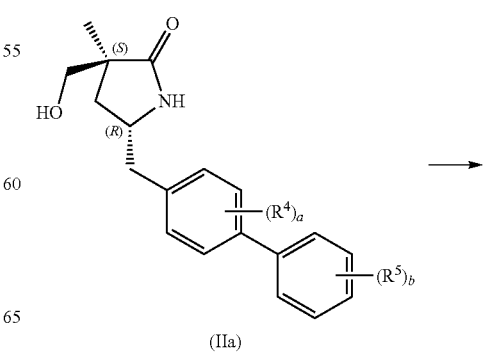

(IIa)

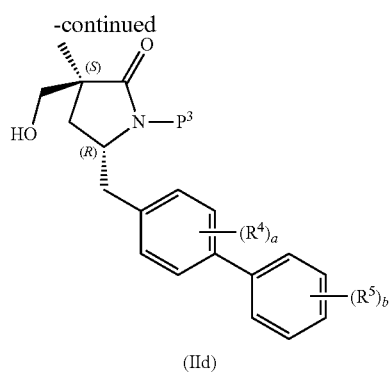

(IId)

This can be accomplished in a manner similar to that described for protecting the amine on the compound of formula IIb to preparing a compound of formula IIc. In one embodiment $P^3$ is t-butoxycarbonyl.

Compounds of Formula III

The invention relates to compounds of formula III and processes for preparing them:

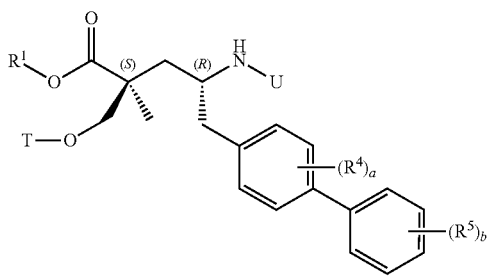

(III)

or a salt thereof. The integer a is 0 or 1, and $R^4$ is selected from halo, —$CH_3$, —$CF_3$, and —CN.

In one particular embodiment, a is 0. The integer b is 0 or an integer from 1 to 3, and each $R^5$ is independently selected from halo, —OH, —$CH_3$, —$OCH_3$, and —$CF_3$. In one particular embodiment, b is 0.

$R^1$ is selected from H, —$C_{1-8}$alkyl, —$C_{1-3}$alkylene-$C_{6-10}$aryl, —$[(CH_2)_2O]_{1-3}CH_3$, —$C_{1-6}$alkylene-$OC(O)R^{10}$, —$C_{1-6}$alkylene-$NR^{11}R^{12}$, —$C_{1-6}$alkylene-$C(O)R^{13}$, —$C_{0-6}$alkylenemorpholinyl, —$C_{1-6}$alkylene-$SO_2$—$C_{1-6}$alkyl,

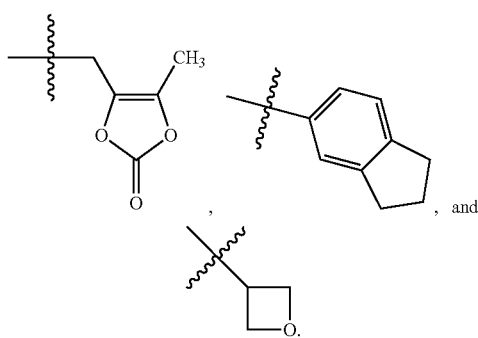

, and

The $R^{10}$ group is selected from —$C_{1-6}$alkyl, —O—$C_{1-6}$alkyl, —O—$C_{3-7}$cycloalkyl, —$CH[CH(CH_3)_2]$—$NH_2$, and —CH[$CH(CH_3)_2$]—$NHC(O)O$—$C_{1-6}$alkyl. The $R^{11}$ and $R^{12}$ groups are —$C_{1-6}$alkyl or are taken together as —$(CH_2)_{3-6}$—, —$C(O)$—$(CH_2)_3$—, or —$(CH_2)_2O(CH_2)_2$—. The $R^{13}$ group is selected from —O—$C_{1-6}$ alkyl, —O-benzyl, and —$NR^{11}R^{12}$. In one particular embodiment, $R^1$ is:

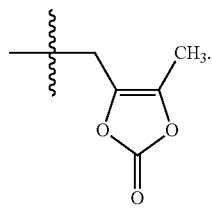 [SMILES: *Cc1oc(=O)oc1C]

T is H or $P^2$, where $P^2$ is an alcohol protecting group. In one particular embodiment, the compounds of formula III are novel compounds and T is $P^2$, for example, tetrahydropyran. This embodiment can be depicted as formula III'

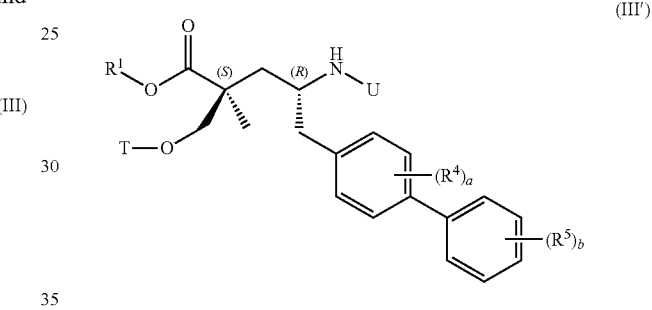

(III')

U is H or $P^3$, where $P^3$ is an amino protecting group. In one particular embodiment, U is H or t-butoxycarbonyl.

Exemplary embodiments include:

compounds of formula IIIa: T is $P^2$; U is $P^3$; and a, b, $R^1$, $R^4$, and $R^5$ are as defined for compounds of formula III;

compounds of formula IIIb: T is H; U is H; and a, b, $R^1$, $R^4$, and $R^5$ are as defined for compounds of formula III;

compounds of formula IIIc: T is $P^2$; U is H; and a, b, $R^1$, $R^4$, and $R^5$ are as defined for compounds of formula III; and compounds of formula IIId: T is H; U is $P^3$; and a, b, $R^1$, $R^4$, and $R^5$ are as defined for compounds of formula III.

The process for preparing a compound of formula IIIa, where $R^1$ is H, involves:

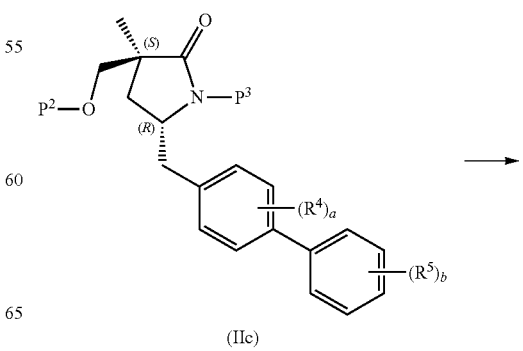

(IIc)

29
-continued

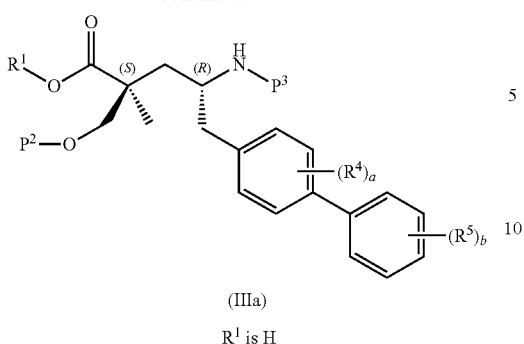

(IIIa)
R¹ is H

This pyrrolidone ring opening reaction involves reacting a compound of formula (IIc) with a base. In one embodiment, the base is lithium hydroxide. This step is typically conducted in a suitable inert diluent such as tetrahydrofuran, and is generally conducted initially at a temperature within the range of about –5 to 5° C., then heated to a temperature within the range of about 25-40° C. In one embodiment P² is tetrahydropyranyl. In another embodiment P³ is t-butoxycarbonyl.

The process for preparing a compound of formula IIIa, where R¹ is not H, i.e., R¹ is —$C_{1-8}$alkyl, —$C_{1-3}$alkylene-$C_{6-10}$aryl, —[(CH$_2$)$_2$O]$_{1-3}$CH$_3$, —$C_{1-6}$alkylene-OC(O)R$^{10}$, —$C_{1-6}$alkylene-NR$^{11}$R$^{12}$, $C_{1-6}$alkylene-C(O)R$^{13}$, —$C_{0-6}$alkylenemorpholinyl, —$C_{1-6}$alkylene-SO$_2$—$C_{1-6}$alkyl,

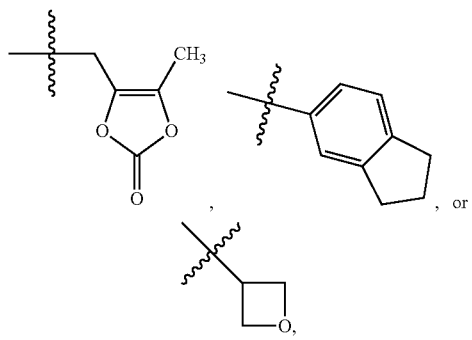

, or involves:

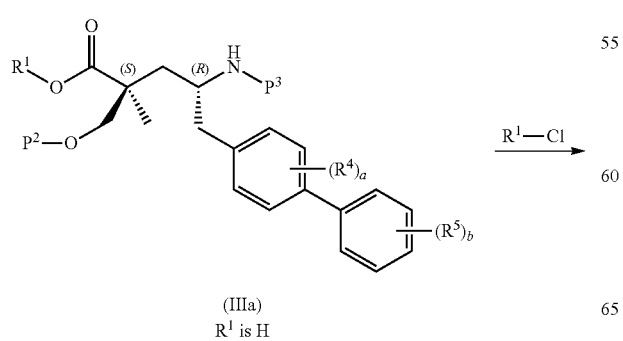

(IIIa)
R¹ is H

30
-continued

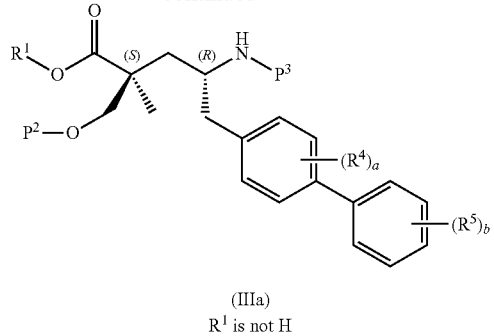

(IIIa)
R¹ is not H

This reaction involves reacting a compound of formula IIIa, where R¹ is H, with a compound of formula R¹—Cl, where R¹ is the desired non-hydrogen moiety, in the presence of a base. In one embodiment, the base is an alkali metal carbonate such as potassium carbonate. In one embodiment, R¹—Cl is 4-chloromethyl-5-methyl-1,3-dioxol-2-one, resulting in R¹ being:

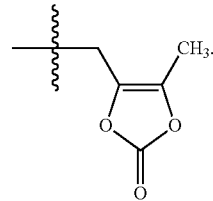 [SMILES: *Cc1oc(=O)oc1C]

This step is typically conducted in a suitable inert diluent such as N,N-dimethylformamide, and is generally conducted initially at a temperature within the range of about –5 to 5° C., then maintained at room temperature until completion. In one embodiment P² is tetrahydropyranyl. In another embodiment P³ is t-butoxycarbonyl.

The process for preparing a compound of formula IIIb involves removal of the P² alcohol protecting group and the P³ amino protecting group:

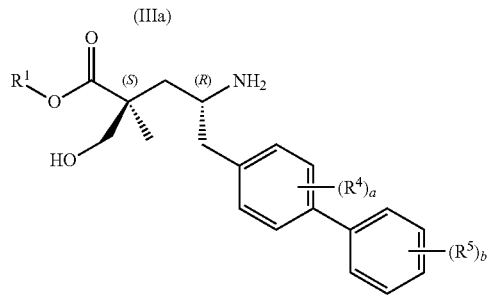

(IIIb)

Generally the deprotection occurs in an ether solvent and is conducted at room temperature. In one embodiment, the ether solvent is cyclopentyl methyl ether. It is preferably, although not required that the $P^2$ and $P^3$ groups are selected so as to be removed by the same reagent. For example, when $P^2$ is an acid-removable alcohol protecting group such as tetrahydropyranyl, and $P^3$ is an acid-removable amino protecting group such as t-butoxycarbonyl, deprotection can occur using a single reagent, for example, hydrochloric acid. This step is typically conducted in a suitable inert diluent such as dichloromethane. In another embodiment, the compound of formula IIIb is prepared as a crystalline material, by adding an inert diluent such as diisopropyl ether to the reaction mixture, and optionally adding seed crystals, followed by filtration, and drying.

The process for preparing a compound of formula IIIc involves protecting the alcohol on the compound of formula IIIb:

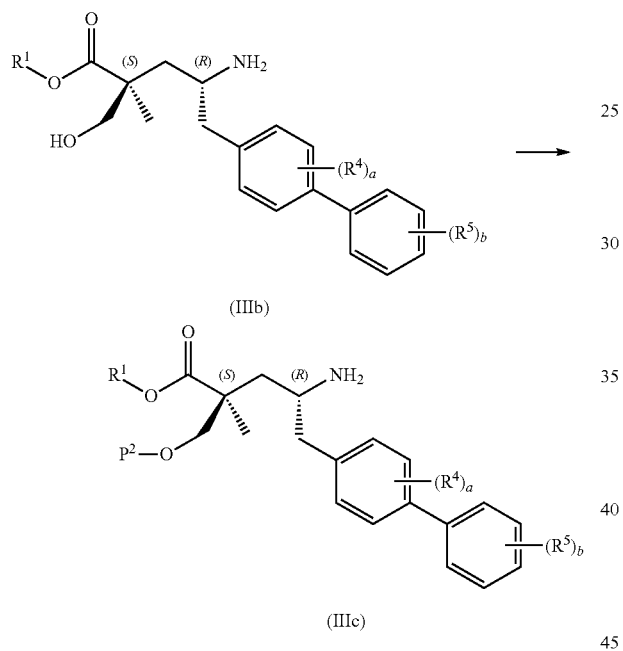

This reaction involves reacting a compound of formula IIIb with an alcohol protecting reagent in the presence of an acid. In one embodiment, the alcohol protecting reagent is dihydropyran, resulting in $P^2$ being tetrahydropyranyl. A particularly suitable acid is p-toluenesulfonic acid. This step is typically conducted in a suitable inert diluent such as dichloromethane, and is generally conducted initially at a temperature within the range of about −5 to 5° C., then at about room temperature. In another embodiment, the compound of formula IIIc is prepared as a crystalline material, by adding an inert diluent such as diisopropyl ether to the reaction mixture, followed by reslurrying, filtration, and drying The process for preparing a compound of formula IIId involves selective removal of the $P^2$ is an alcohol protecting group of a compound of formula IIIa:

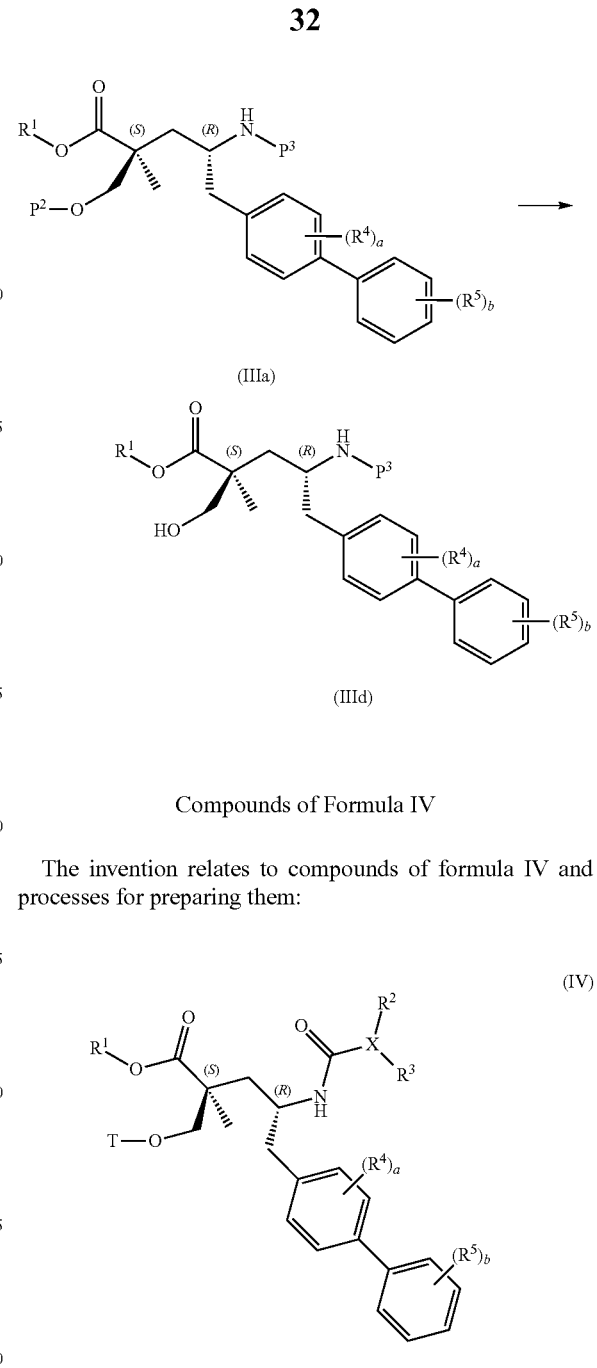

Compounds of Formula IV

The invention relates to compounds of formula IV and processes for preparing them:

(IV)

or a tautomer or salt thereof.

$R^1$ is selected from H, —$C_{1-8}$alkyl, —$C_{1-3}$alkylene-$C_{6-10}$aryl, —[$(CH_2)_2O]_{1-3}CH_3$, —$C_{1-6}$alkylene-OC(O)$R^{10}$, —$C_{1-6}$alkylene-NR$^{11}$R$^{12}$, —$C_{1-6}$alkylene-C(O)R$^{13}$, —$C_{0-6}$alkylenemorpholinyl, —$C_{1-6}$alkylene-SO$_2$—$C_{1-6}$alkyl,

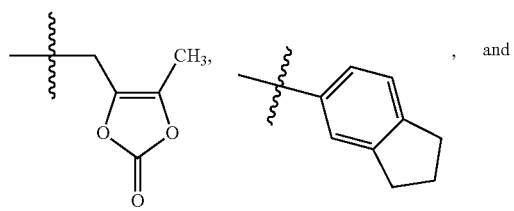

, and

-continued

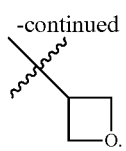

The $R^{10}$ group is selected from —$C_{1-6}$alkyl, —O—$C_{1-6}$alkyl, —O—$C_{3-7}$cycloalkyl, —CH[CH(CH$_3$)$_2$]—NH$_2$, and —CH[CH(CH$_3$)$_2$]—NHC(O)O—$C_{1-6}$alkyl. The $R^{11}$ and $R^{12}$ groups are —$C_{1-6}$alkyl or are taken together as —(CH$_2$)$_{3-6}$—, —C(O)—(CH$_2$)$_3$—, or —(CH$_2$)$_2$—O—(CH$_2$)$_2$—. The $R^{13}$ group is selected from —O—$C_{1-6}$alkyl, —O-benzyl, and —NR$^{11}$R$^{12}$. In one particular embodiment, R$^1$ is:

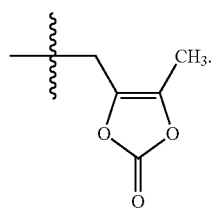 [SMILES: *Cc1oc(=O)oc1C]

In addition, each alkyl group in R$^1$ is optionally substituted with 1 to 8 fluoro atoms. For example, R$^1$ can be —$C_{1-8}$alkyl or a group such as —CH(CH$_3$)CF$_3$, —CH$_2$CF$_2$CF$_3$, —CH(CF$_3$)$_2$, —(CH$_2$)$_2$CF$_3$, —CH(CH$_2$F)$_2$, —C(CF$_3$)$_2$CH$_3$, or —CH(CH$_3$)CF$_2$CF$_3$.

X is selected from pyrazole, imidazole, triazole, benzotriazole, tetrazole, oxazole, isoxazole, thiazole, pyrimidine, pyridazine, benzimidazole, pyran, and pyridyltriazole. In one particular embodiment, X is triazole.

The R$^2$ may be absent. When present, R$^2$ is attached to a carbon atom in the X ring and is selected from H; halo; —C$_{0-5}$alkylene-OH; —C$_{1-6}$alkyl; —C$_{3-7}$cycloalkyl; —C$_{0-2}$alkylene-O—C$_{1-6}$alkyl; —C(O)C$_{1-6}$alkyl; —C$_{0-1}$alkylene-COOH; —C(O)NR$^{20}$R$^{21}$; —NHC(O)-phenylene-OCH$_3$; =O; phenyl optionally substituted with one or two groups independently selected from halo, —OH, and —OCH$_3$; pyridinyl; and pyrazinyl. The R$^{20}$ group is H or —C$_{1-6}$alkyl. The R$^{21}$ group is selected from H, —C$_{1-6}$alkyl, —(CH$_2$)$_2$OH, —(CH$_2$)$_2$OCH$_3$, —(CH$_2$)$_2$SO$_2$NH$_2$, and —C$_{0-1}$alkylene-C$_{3-7}$cycloalkyl. Alternately, the R$^{20}$ and R$^{21}$ groups are taken together to form a saturated or partially unsaturated —C$_{3-5}$heterocycle optionally substituted with halo or —OH, and optionally containing an oxygen atom in the ring. In addition, each alkyl group in R$^2$ is optionally substituted with 1 to 8 fluoro atoms. For example, R$^2$ can be —$C_{1-6}$alkyl or a group such as —CH(CH$_3$)CF$_3$, —CH$_2$CF$_2$CF$_3$, —CH(CF$_3$)$_2$, —(CH$_2$)$_2$CF$_3$, —CH(CH$_2$F)$_2$, —C(CF$_3$)$_2$CH$_3$, or —CH(CH$_3$)CF$_2$CF$_3$. In one particular embodiment, R$^2$ is H.

R$^3$ can be attached to a carbon or nitrogen atom in the X ring, and is selected from H; —OH; —C$_{1-6}$alkyl; —C$_{1-2}$alkylene-COOH; —CH$_2$OC(O)CH(R$^{30}$)NH$_2$; —CH[CH(CH$_3$)$_2$]—NHC(O)O—C$_{1-6}$alkyl; pyridinyl; and phenyl or benzyl optionally substituted with one or more groups selected from halo and —OCH$_3$. In addition, when R$^3$ is attached to nitrogen atom, R$^3$ can be P$^4$, where P$^4$ is an amino protecting group. The R$^{30}$ group is selected from H, —CH(CH$_3$)$_2$, phenyl, and benzyl. In addition, each alkyl group in R$^3$ is optionally substituted with 1 to 8 fluoro atoms. For example, R$^3$ can be —$C_{1-6}$alkyl or a group such as —CH(CH$_3$)CF$_3$, —CH$_2$CF$_2$CF$_3$, —CH(CF$_3$)$_2$, —(CH$_2$)$_2$CF$_3$, —CH(CH$_2$F)$_2$, —C(CF$_3$)$_2$CH$_3$, or —CH(CH$_3$)CF$_2$CF$_3$. In one particular embodiment, R$^3$ is trityl.

The integer a is 0 or 1, and R$^4$ is selected from halo, —CH$_3$, —CF$_3$, and —CN. In one particular embodiment, a is 0.

The integer b is 0 or an integer from 1 to 3, and each R$^5$ is independently selected from halo, —OH, —CH$_3$, —OCH$_3$, and —CF$_3$. In one particular embodiment, b is 0.

P$^2$ is an alcohol protecting group. In one particular embodiment, T is H or tetrahydropyran.

The process for preparing a compound of formula IV involves the following coupling reaction:

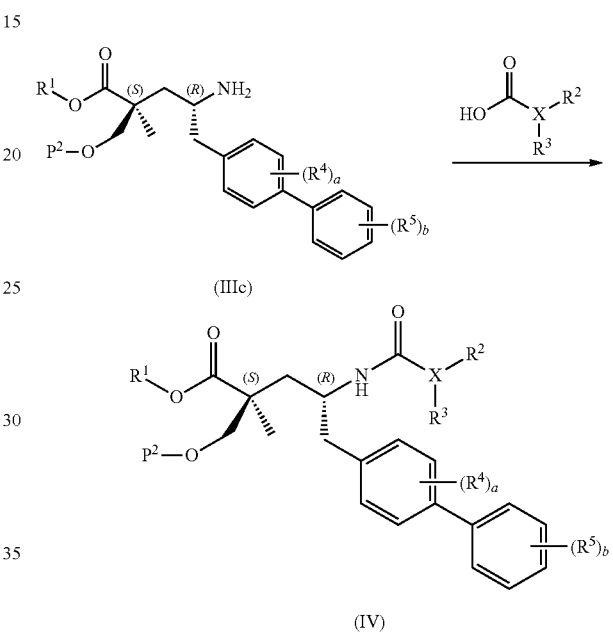

This reaction involves coupling a compound of formula IIIc with HOOC—XR$^2$R$^3$ with a suitable carboxylic acid/amine coupling reagent. This step is conducted in an inert diluent in the presence of a base such as N,N-diisopropylethylamine, and is performed under conventional amide bond-forming conditions. In one embodiment, the coupling reagent is HCTU. This step is typically conducted in a suitable inert diluent such as tetrahydrofuran, and is generally conducted at a temperature within the range of about −5 to 5° C., for example, at 0° C. In one embodiment, HOOC—XR$^2$R$^3$ is:

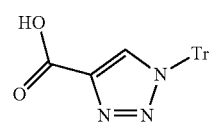

where Tr is trityl. In another embodiment, the compound of formula IV is prepared as a crystalline material, by reslurrying in an inert diluent such as methanol, followed by filtration and drying.

The P$^2$ alcohol protecting group on the compound of formula IV can then be removed:

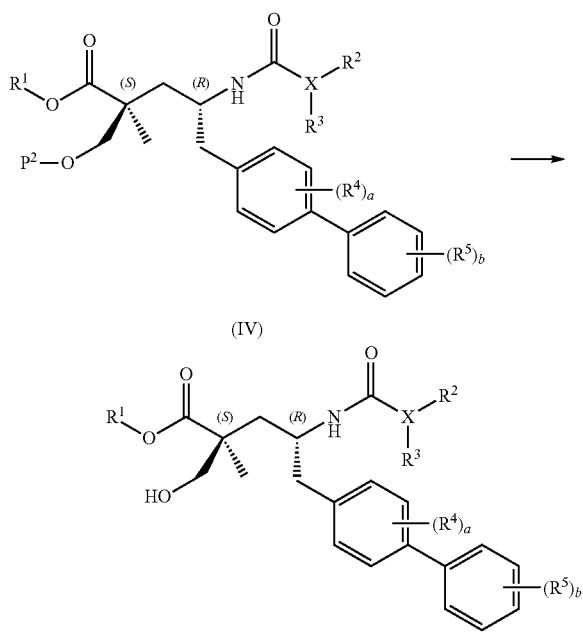

(IV)

Generally the deprotection is conducted at room temperature using a suitable deprotecting agent. For example, when $P^2$ is an acid-removable alcohol protecting group such as tetrahydropyranyl, deprotection can occur using an acid such as hydrochloric acid. In another embodiment, the product is prepared as a crystalline material, by including an inert diluent such as methanol in the deprotection step, and optionally adding seed crystals, followed by filtration, and drying.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard generally accepted meaning:

AcOH acetic acid
CPME cyclopentyl methyl ether
DCM dichloromethane or methylene chloride
DIPEA N,N-diisopropylethylamine
DMAP 4-dimethylaminopyridine
DMF N,N-dimethylformamide
EDCI N-(3-dimethylaminopropyl)-N'-ethylcarbodiimide
EtOAc ethyl acetate
HCTU (2-(6-chloro-1H-benzotriazole-1-yl)-1,1,3,3-tetramethylaminium hexafluorophosphate)
MeCN acetonitrile
MeOH methanol
MeTHF 2-methyltetrahydrofuran
NaHMDS sodium hexamethyldisilazide
NMM N-methylmorpholine
TFA trifluoroacetic acid
THF tetrahydrofuran Unless noted otherwise, all materials, such as reagents, starting materials and solvents, were purchased from commercial suppliers (such as Sigma-Aldrich, Fluka Riedel-de Haën, Strem Chemicals, Inc., and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% water/2% MeCN/1.0 mL/L TFA; solvent B was 90% MeCN/10% water/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

[(R)-1-Biphenyl-4-ylmethyl-2-(2,2,5-trimethyl-4,6-dioxo-[1,3]dioxan-5-yl)-ethyl]-carbamic Acid t-butyl Ester

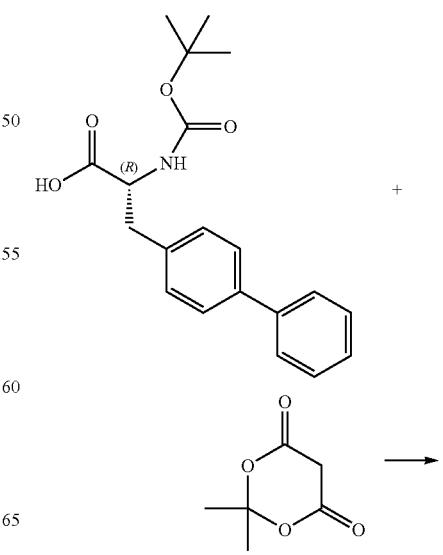

-continued

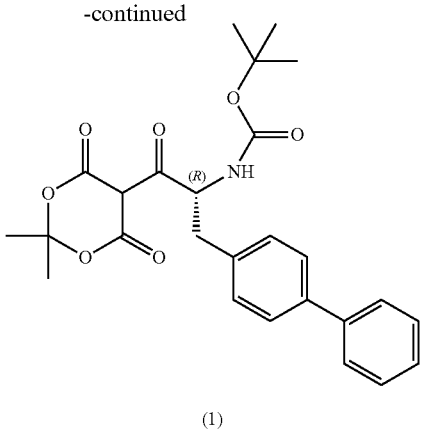

(1)

(R)-3-Biphenyl-4-yl-2-t-butoxycarbonylamino-propionic acid (5.0 g, 15 mmol) and 2,2-dimethyl-1,3-dioxane-4,6-dione (2.3 g, 16.1 mmol) were combined in DMAP (3.2 g, 26.4 mmol). Additional DMAP (2.0 g, 16.1 mmol) and DCM (50 mL) was added and the resulting mixture was stirred and cooled to −5° C. (nitrogen purge) for 30 minutes. EDCI (HCl; (3.1 g, 16.1 mmol) was added in portions, while maintaining the internal temperature below 0° C. with stirring. The mixture was then cooled to −5° C., stirred at that temperature for 3 hours, then left at −20° C. overnight. The mixture was then washed with 0.4 M aqueous KHSO$_4$ (80 mL) and saturated aqueous NaCl (20 mL), then dried over MgSO$_4$ overnight. The solids were filtered off and the filtrate was then evaporated to dryness to yield crude Compound 1 (3.2 g).

AcOH (8.6 mL) was added to a solution of crude Compound 1 (6.4 g, 14 mmol, 1.0 eq.) in anhydrous MeCN (90 mL) was added AcOH (8.6 mL) at −5° C. under nitrogen. The mixture was stirred at −5° C. for 30 minutes, then sodium borohydride (1.3 g, 34.5 mmol, 2.5 eq.) was added in small portions over 2 hours. After stirring for another 1 hour at −5° C., saturated aqueous NaCl and 1.7 M of NaCl in water (30 mL) was added. The layers were separated and the organic layer was washed with saturated aqueous NaCl (2×30 mL) and water (2×30 mL), dried under MgSO$_4$, filtered and evaporated. The resulting crude product was further purified by chromatography (5:1 heptane:EtOAc) to yield Compound 2 (1.1 g, 98.4% purity) as a light yellow solid.

Compound 2 (5.0 g, 11 mmol, 1.0 eq.) and K$_2$CO$_3$ (1.8 g, 13.2 mmol, 1.2 eq.) were dissolved in DMF (33.9 mL) and cooled to 0° C. with stirring under nitrogen. Methyl iodide (892 µL, 1.3 eq.) was added and the resulting mixture was stirred at 0° C. for 1 hour. The mixture was allowed to warm to room temperature (23° C.) and held overnight. Saturated aqueous NaCl (35 mL) and EtOAc (35 mL) were added, and the resulting mixture was stirred for 2 minutes. The layers were separated and the organic layer was evaporated. The residue was triturated with EtOAc (20 mL). The solid was filtered off and dried under vacuum. The filtrate was concentrated and triturated again with EtOAc to yield the title compound (3.9 g).

Example 1

(3R,5R)-5-Biphenyl-4-ylmethyl-3-methyl-2-oxo-pyrrolidine-3-carboxylic Acid (1) ⟶

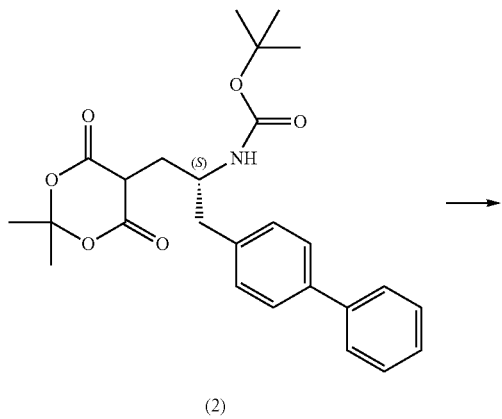

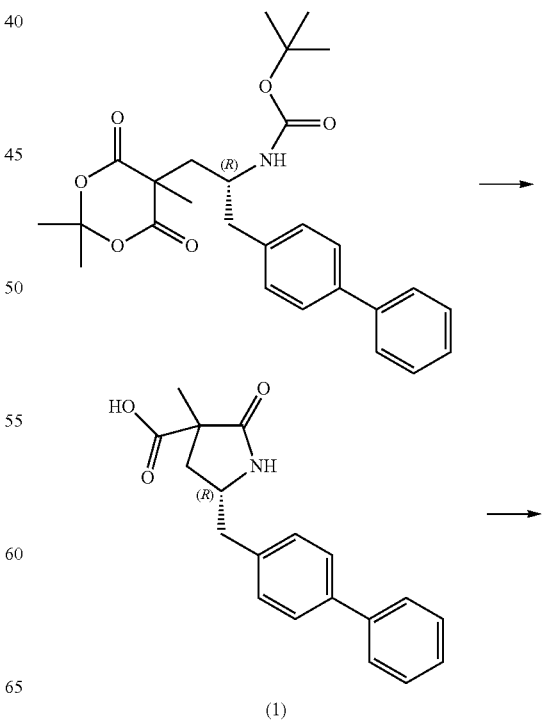

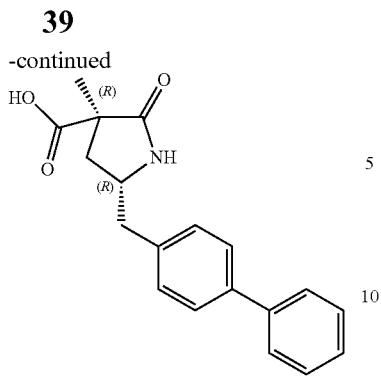

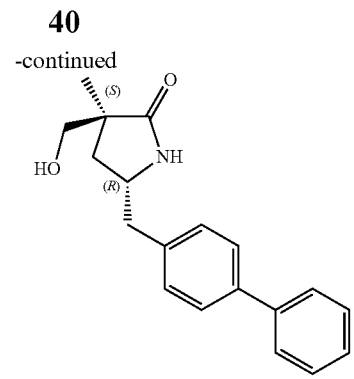

iBu = isobutyl

[(R)-1-Biphenyl-4-ylmethyl-2-(2,2,5-trimethyl-4,6-dioxo-[1,3]dioxan-5-yl)-ethyl]-carbamic acid t-butyl ester (400.0 g, 855.5 mmol) was combined with CPME (2 L) to form a slurry. The slurry was cooled at 0° C. and 3.0 M HCl in CPME (2.0 L) was added. The resulting mixture was stirred at room temperature for 24 hours, yielding a free flowing slurry. Filtration and drying yielded Compound 1 as a 93:7 mixture of diastereoisomers (206 g total). Reslurrying in MeTHF (1 L) at room temperature followed by the addition of CPME (1 L; slurry overnight at room temperature) yielded the title compound (170 g; 98% de purity).

(3R,5R)-5-Biphenyl-4-ylmethyl-3-methyl-2-oxo-pyrrolidine-3-carboxylic acid (25.0 g, 80.8 mmol) was combined with THF (500 mL) and NMM (25 mL, 230 mmol). The resulting mixture was cooled at 0° C. (jacket temp set at −5° C.) and isobutyl chloroformate (21.0 mL, 162 mmol) was added dropwise via addition funnel, while maintaining the internal temperature below 5° C.). The mixture was stirred at 0° C. for 20 minutes. Sodium borohydride (12.2 g, 323 mmol) dissolved in water (40 mL) was added dropwise and the mixture was stirred at 0° C. for 20 minutes (>98% conversion). The reaction was quenched with 1M aqueous HCl (300 mL) and the mixture was stirred at room temperature for 1 hour. Most of solvent was distilled off, leaving a white slurry. The slurry was stirred for 60 minutes and then filtered (small particles, slow filtration) to yield the title compound as a white solid (23 g; >98% purity).

Example 2

(3S,5R)-5-Biphenyl-4-ylmethyl-3-hydroxymethyl-3-methyl-pyrrolidin-2-one

Example 3

(2S,4R)-5-Biphenyl-4-yl-4-t-butoxycarbonylamino-2-methyl-2-(tetrahydro-pyran-2-yloxymethyl)-pentanoic Acid

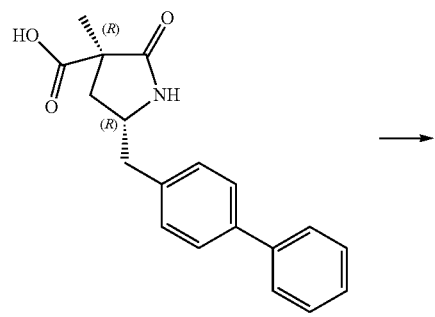

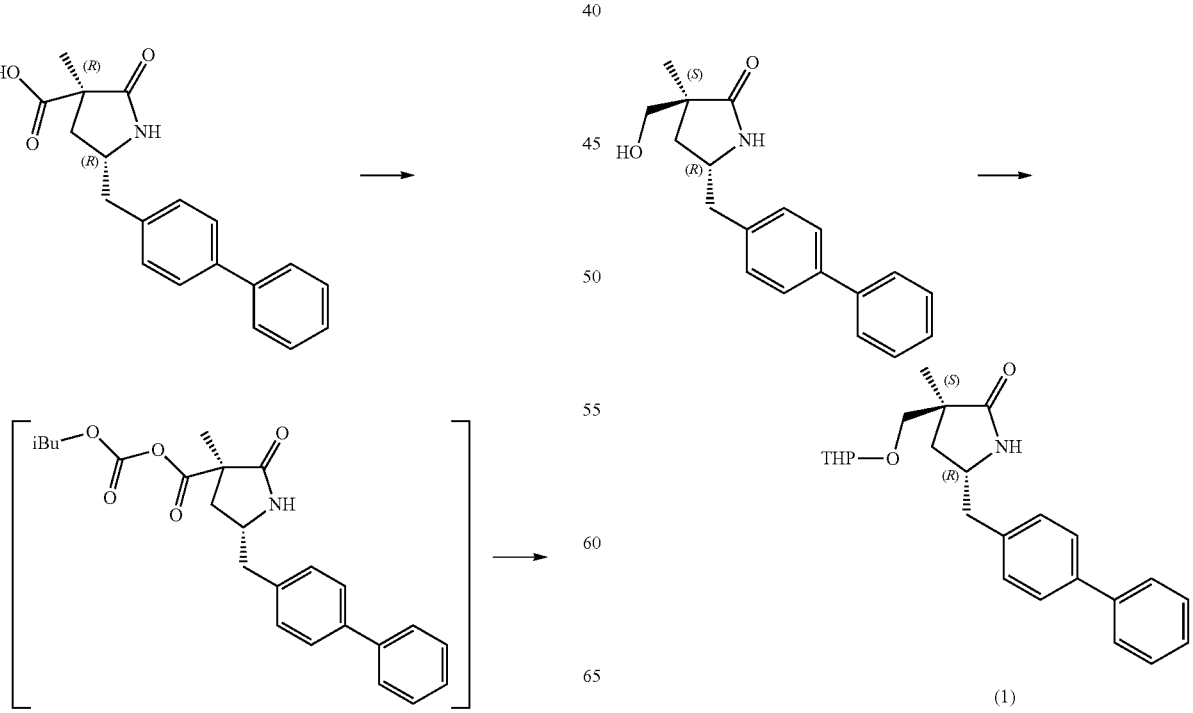

(1)

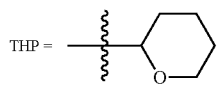
THP =

(3S,5R)-5-Biphenyl-4-ylmethyl-3-hydroxymethyl-3-methyl-pyrrolidin-2-one (300 g, 1.0 mol) and DCM (3.8 L) were combined and the resulting mixture was cooled at 0° C. Dihydropyran (185 mL, 2.0 mol) and p-toluenesulfonic acid (52.5 g, 305 mmol) were added and the mixture was stirred at room temperature for 2 hours. Aqueous s NaHCO$_3$ (10:90, NaHCO$_3$:water, 3 L) was added and the phases were separated. The organic layer was dried with Na$_2$SO$_4$ followed by solvent removal to approximately 500 mL. Into the crude product was added diisopropyl ether (2 L) and seed crystals. The resulting slurry was stirred overnight at room temperature. Filtration and drying yielded crystalline Compound 1 (320 g; >98% purity).

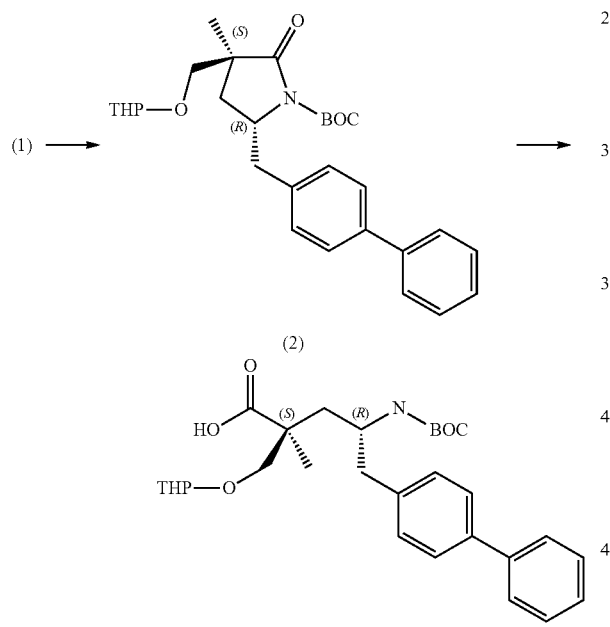

BOC = t-butoxycarbonyl

Compound 1 (320.0 g, 843.2 mmol) was dissolved in THF (2.5 L) to yield a clear solution, which was purged with nitrogen. The solution was cooled at 0° C. and 1.0 M NaHMDS in THF (920 mL, 920 mmol) was added dropwise over 30 minutes. The mixture was stirred at 0° C. for 15 minutes then di-t-butyldicarbonate (202 g, 926 mmol) dissolved in THF (500 mL) was added dropwise over 1 hour, while maintaining the internal temperature below 5° C. The mixture was allowed to warm to room temperature (>99% conversion to Compound 2). The mixture was cooled to <5° C. followed by the addition of 1.0 M aqueous LiOH (2.5 L, 2.5 mol). The cooling bath was removed and the mixture was stirred overnight at 27° C. (~4% starting material remaining). The mixture was heated at 35° C. for 4 hours (>98% conversion), then cooled to 15° C. The mixture was diluted with EtOAc (3 L) and saturated aqueous NH$_4$Cl (0.37:0.63, NH$_4$Cl:water, 3 L). The phases were separated, and the organic layer was washed with saturated aqueous NH$_4$Cl (3 L) and saturated aqueous NaCl (3 L). The organic layer dried with Na$_2$SO$_4$ (1 kg), followed by solvent removal to yield the crude title compound (463 g) as a glassy sticky solid.

Example 4

(2S,4R)-5-Biphenyl-4-yl-2-hydroxymethyl-2-methyl-4-[(1H-[1,2,3]triazole-4-carbonyl)-amino]-pentanoic Acid 5-Methyl-2-oxo-[1,3]dioxol-4-ylmethyl Ester

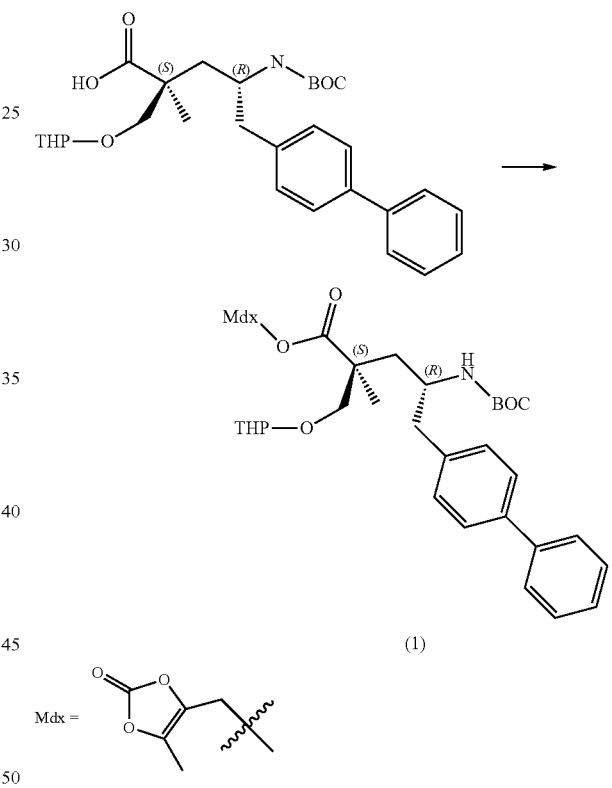

(2S,4R)-5-Biphenyl-4-yl-4-t-butoxycarbonylamino-2-methyl-2-(tetrahydro-pyran-2-yloxymethyl)-pentanoic acid (79.4 g; crude) was dissolved in DMF (640 mL). K$_2$CO$_3$ (23.8 g, 172 mmol) was added and the resulting mixture was stirred at room temperature for 15 minutes. The mixture was cooled at 0° C. followed by addition of 4-chloromethyl-5-methyl-1,3-dioxol-2-one (20.6 mL, 188 mmol). The mixture was maintained at 0° C. and stirred over 3 hours (~55% starting material and ~38% product). The mixture was then stirred at room temperature (20.2° C.) overnight (~16 hours; starting material was non-detectable). EtOAc (1.5 L) was added. The organic layer was washed with 3 M aqueous NH$_4$Cl (2×1.5 L) and saturated aqueous NaCl (1.5 L), dried with Na$_2$SO$_4$ (40 g), followed by solvent removal to yield crude Compound 1 as a thick oil.

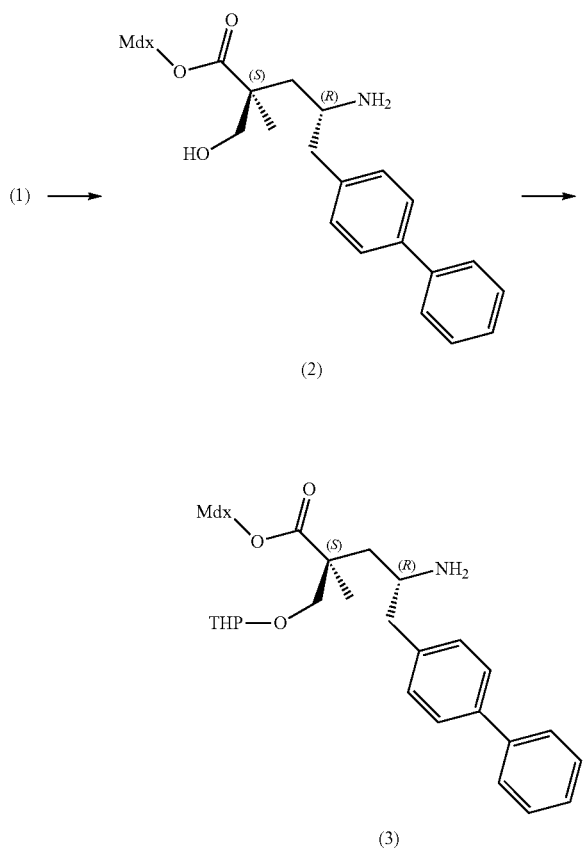

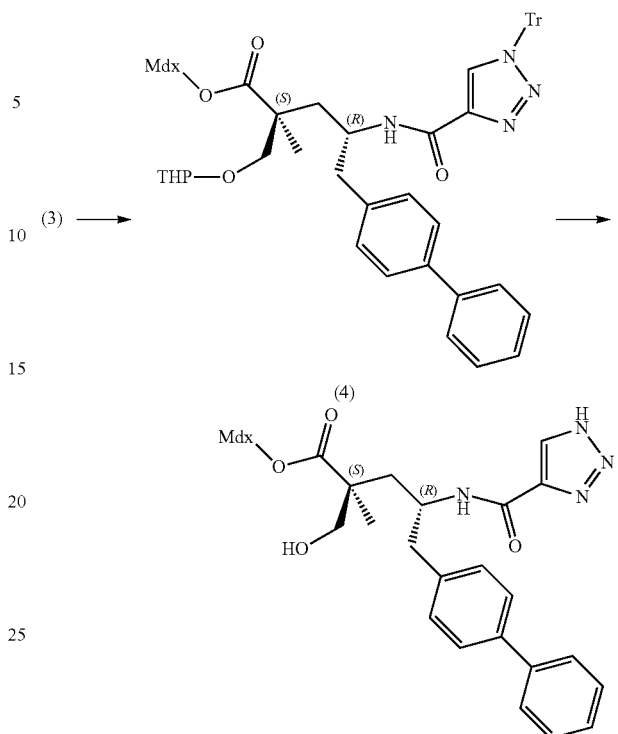

Tr = trityl

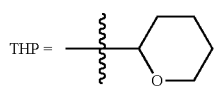
THP =

Crude Compound 1 was dissolved in DCM (500 ml) followed by the addition of 3.0 M aqueous HCl in CPME (798 mL, 2.4 mol). Seed crystals were added and the resulting mixture was stirred overnight to yield a free flowing slurry. The volume was reduced by half and the resulting slurry was filtered, flasked, and the filter cake was washed with diisopropyl ether to yield the Compound 2 as a off-white solid HCl crystalline salt (69.1 g; 96.2% purity).

Compound 2 (350 g, 757.7 mmol) and DCM (4 L) were combined and the resulting mixture was cooled at 0° C. Dihydropyran (173 mL, 1.9 mol) and p-toluenesulfonic acid (19.6 g, 113.6 mmol) were added and the mixture was stirred at 0° C. for 18 hours (>95% conversion). Diisopropyl ether (2 L) was added and the solution was concentrated by rotary evaporation. The resulting slurry was stirred at 4° C. for 4 hours. Filtration and drying yielded Compound 3 (312 g; >98% purity).

1-Trityl-1H-1,2,3-triazole-4-carboxylic acid (2823 g, 796 mmol) was dissolved in THF (6 L). DIPEA (330 mL, 1.9 mol) was added and the resulting mixture was cooled to 0° C. HCTU (380 g, 918 mmol) was added in portions and the mixture was stirred at 0° C. for 15 minutes. Compound 3 (312 g, 612 mmol) was added and the resulting mixture was stirred at 0° C. for 30 minutes (complete conversion). The reaction was quenched with water (5 L) followed by the addition of EtOAc (5 L). The phases were separated, and the organic layer was washed with saturated aqueous NaCl (5 L), dried with $Na_2SO_4$, and concentrated by rotary evaporation. The crude product was reslurried in 5 volumes of MeOH to yield Compound 4 as a crystalline material (400 g; >98% purity).

Compound 4 (40.0 g, 47.2 mmol) was dissolved in 1.25 M HCl in MeOH (200 mL) and stirred to aid dissolution (>95% deprotection after 2 hours at room temperature). Water (200 mL) was slowly added until the solution became cloudy (100 mL). Seed crystals were added and the solution was stirred at room temperature for 30 minutes to yield a free-flowing slurry. The remaining water was added dropwise and stirred at room temperature overnight. Filtration and drying yielded the title compound as intermediate grade material (30 g). This material was suspended in EtOAc (150 mL) and stirred for 30 minutes. Hexanes (150 mL) was added slowly via addition funnel and the resulting free-flowing slurry was stirred at room temperature overnight. Filtration and drying yielded the title compound as a crystalline material (15.3 g; 99.1% purity).

It is understood that compounds such as this can exist in a tautomer form, for example, as (2S,4R)-5-biphenyl-4-yl-2-hydroxymethyl-2-methyl-4-[(3H-[1,2,3]triazole-4-carbonyl)-amino]-pentanoic acid 5-methyl-2-oxo-[1,3]dioxol-4-ylmethyl ester.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A process for preparing a compound of formula I:

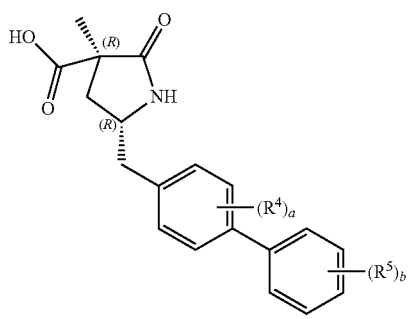

(I)

or a salt thereof, where a is 0 or 1; $R^4$ is selected from halo, —CH$_3$, —CF$_3$, and —CN; b is 0 or an integer from 1 to 3; and each $R^5$ is independently selected from halo, —OH, —CH$_3$, —OCH$_3$, and —CF$_3$; the process comprising the step of reslurrying a compound of formula (1):

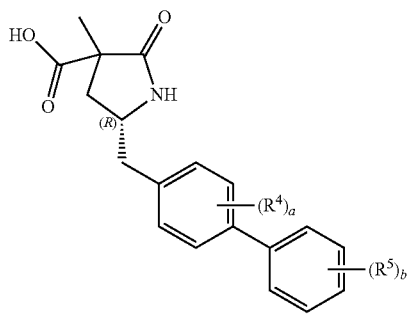

(1)

in an ether solvent to form a compound of formula I or a salt thereof.

2. The process of claim 1, where the ether solvent is 2-methyltetrahydrofuran.

3. The process of claim 2, where the ether solvent further comprises cyclopentyl methyl ether.

4. The process of claim 1, where the compound of formula (1) is prepared by the acidic deprotection of a compound of formula (2):

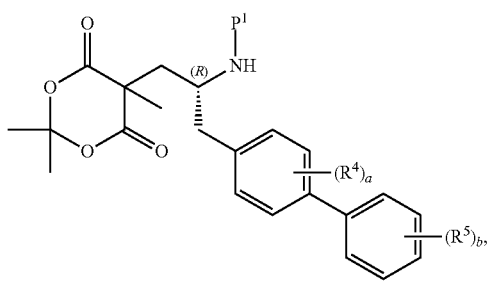

(2)

where $P^1$ is an amino protecting group.

5. The process of claim 4, where acidic deprotection is conducted with 3M HCl.

6. The process of claim 4, where $P^1$ is selected from acetyl, adamantyl-oxycarbonyl, t-amyloxycarbonyl, benzothiophene sulfone-2-methoxycarbonyl, benzoyl, benzyl, benzyloxycarbonyl, 2-(p-biphenylyl)propyl-2-oxycarbonyl, t-butoxycarbonyl, 2-(t-butylsulfonyl)-2-propenyloxycarbonyl, 3,4-dimethoxybenzyl, 2,2-dimethyl-3,5-dimethyloxybenzyloxycarbonyl, dithiasuccinoyl, formyl, 9-fluorenylmethoxycarbonyl, 2-furanmethyloxycarbonyl, p-methoxybenzyl, p-methoxybenzyl carbonyl, 1-methylcyclobutyloxycarbonyl, o-nitrophenylsulfenyl, 2-phenylpropyl-2-oxycarbonyl, 2-(p-phenylazophenyl)propyl-2-oxycarbonyl, silyl ethers, tosyl, trifluoroacetyl, β-trimethylsilylethyloxycarbonyl, triphenylmethyl, and trityl.

7. The process of claim 6, where $P^1$ is t-butoxycarbonyl.

8. A process for preparing a compound of formula IIa:

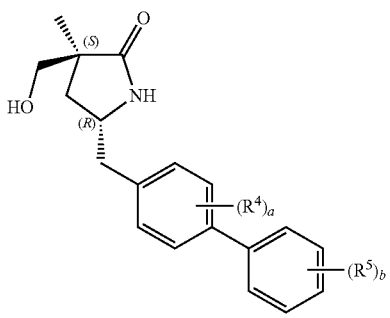

(IIa)

or a salt thereof, where a is 0 or 1; $R^4$ is selected from halo, —CH$_3$, —CF$_3$, and —CN; b is 0 or an integer from 1 to 3; and each $R^5$ is independently selected from halo, —OH, —CH$_3$, —OCH$_3$, and —CF$_3$; the process comprising the steps of (a) activation of the carboxyl group of a compound of formula I:

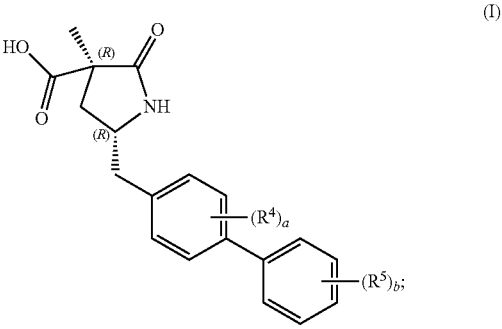

(I)

and (b) reacting the resulting product with a reducing agent to form a compound of formula IIa or a salt thereof.

9. The process of claim 8, where step (a) is conducted with isobutyl chloroformate in the presence of a tertiary amine base.

10. The process of claim 9, where the tertiary amine base is N-methylmorpholine.

11. The process of claim 8, where the reducing agent is sodium tetrahydroborate.

12. The process of claim 1, where the ether solvent is diisopropyl ether.

* * * * *